United States Patent
Pfirrmann

(10) Patent No.: US 10,968,190 B2
(45) Date of Patent: Apr. 6, 2021

(54) PROCESSES FOR PREPARING OXATHIAZIN-LIKE COMPOUNDS

(71) Applicant: GEISTLICH PHARMA AG, Wolhusen (CH)

(72) Inventor: Rolf W. Pfirrmann, Weggis (CH)

(73) Assignee: GEISTLICH PHARMA AG, Wolhusen (CH)

( * ) Notice: Subject to any disclaimer, the term of this patent is extended or adjusted under 35 U.S.C. 154(b) by 0 days.

(21) Appl. No.: 16/538,344

(22) Filed: Aug. 12, 2019

(65) Prior Publication Data

US 2019/0389819 A1 Dec. 26, 2019

Related U.S. Application Data

(62) Division of application No. 15/535,266, filed as application No. PCT/IB2015/059741 on Dec. 17, 2015, now Pat. No. 10,392,355.

(60) Provisional application No. 62/094,580, filed on Dec. 19, 2014.

(51) Int. Cl.
  *C07D 291/06* (2006.01)
  *A61P 35/00* (2006.01)
  *C07D 419/06* (2006.01)

(52) U.S. Cl.
  CPC ............ *C07D 291/06* (2013.01); *A61P 35/00* (2018.01); *C07D 419/06* (2013.01)

(58) Field of Classification Search
  CPC ...... C07D 291/06; C07D 419/06; A61P 35/00
  USPC ...................................................... 514/222.5
  See application file for complete search history.

(56) References Cited

U.S. PATENT DOCUMENTS 4,829,079 A    5/1989   Toja et al.

FOREIGN PATENT DOCUMENTS

| JP | 2010-536754 A | 12/2010 |
|---|---|---|
| WO | 2006/033446 A1 | 3/2006 |
| WO | 2009/023232 A1 | 2/2009 |
| WO | 2012024083 A1 | 2/2012 |
| WO | 2013190355 A1 | 12/2013 |

OTHER PUBLICATIONS

Office Action issued for Indian Patent Application No. 201737024698 dated Oct. 24, 2019, 6 pages.
International Search Report cited in PCT/IB2015/059741 dated Feb. 24, 2016, 6 pages.
English language translation First Office Action cited in Chinese Application No. 201580072835.0 dated May 23, 2018, 14 pages.
Office Action issued for European patent Application No. 15821172.2 dated Oct. 18, 2018, 7 pages.
Office Action issued for Brazilian Patent Application No. BR112017013188-9 dated Sep. 15, 2020, 8 pages.

*Primary Examiner* — Kahsay Habte

(74) *Attorney, Agent, or Firm* — Rothwell, Figg, Ernst & Manbeck, P.C.

(57) ABSTRACT

Methods for producing compounds useful in reactions to produce oxathiazin-like compounds are disclosed including a process of adding sodium 2-bromoethanesulfonate to a solution of benzyl alcohol and sodium benzyloxide to for mixture, boiling the mixture to reflux four times, concentrating under vacuum until dry, boiling with ethyl alcohol, filtering the ethyl alcohol, and concentrating to dryness to obtain solid sodium 2-benzyletherethanesulfonate.

20 Claims, 12 Drawing Sheets

PROCESSES FOR PREPARING OXATHIAZIN-LIKE COMPOUNDS

BACKGROUND OF THE INVENTION

Field of the Invention

The present invention relates to new compounds, processes for preparing new compounds and uses thereof.

Description of the Background Art

Oxathiazin-like compounds are known from U.S. Pat. Nos. 3,202,657 and 3,394,109.

There remains a need in the art for new compounds and processes for making such compounds to provide compounds with more potent antineoplastic and antimicrobial activity, less toxicity and side effects, and less resistance to treatment by tumor or microbial cells.

SUMMARY OF THE INVENTION

In accordance with the present invention, new oxathiazin-like compounds, processes for making new oxathiazin-like compounds, compounds useful for making oxathiazin-like compounds, and their uses are disclosed.

DETAILED DESCRIPTION OF THE INVENTION

Figure 1:
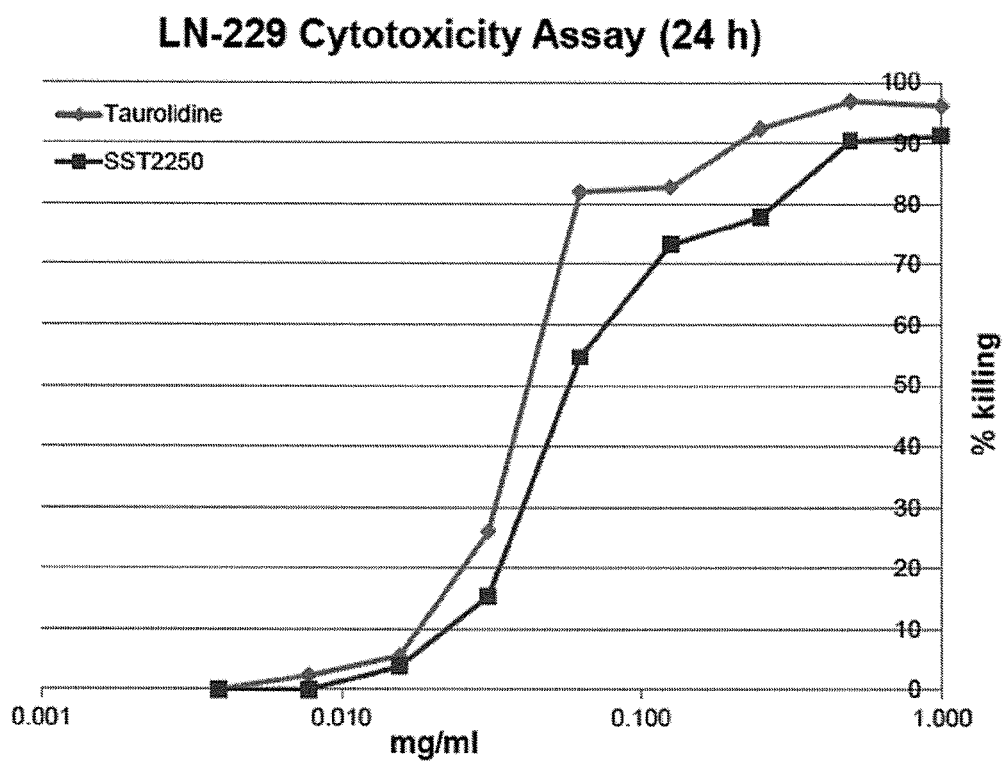
FIG. 1 graphically shows anti-neoplastic activity of one embodiment of the invention in a cytotoxicity assay in LN-229 cells.

According to certain embodiments, the present invention relates to oxathiazin-like compounds, as well as derivatives thereof and processes and compounds for preparing oxathiazin-like compounds and derivatives thereof.

Oxathiazin-like compounds and derivatives thereof according to certain embodiments of the present invention have antineoplastic activities, antimicrobial activities and/or other activities.

Processes for making oxathiazin-like compounds and derivatives thereof according to certain embodiments of this invention provide advantageous methods for making compounds having antineoplastic activities, antimicrobial activities and/or other activities. In certain embodiments, oxathiazin-like compounds and derivatives thereof are useful, inter alia, in the treatment of cancers and tumors in a subject, such as a human patient. Accordingly, in certain embodiments the present invention also relates to treatment of cancers and tumors using compounds described herein. Cancers such as central nervous system cancers including glioblastoma, glioma, neuroblastoma, astrocytoma, and carcinomatous meningitis, colon cancer, rectal cancer and colo-rectal cancer, ovarian cancer, breast cancer, prostate cancer, lung cancer, mesothelioma, melanoma, renal cancer, liver cancer, pancreatic cancer, gastric cancer, esophageal cancer, urinary bladder cancer, cervical cancer, cardiac cancer, gall bladder cancer, skin cancer, bone cancer, cancers of the head and neck, leukemia, lymphoma, lymphosarcoma, adenocarcinoma, fibrosarcoma, and metastases thereof, for example, are diseases contemplated for treatment according to certain embodiments of the invention. Drug resistant tumors, for example a multiple drug resistant (MDR) tumor, also are useful in certain embodiments using the inventive compounds, including drug resistant tumors which are solid tumors, non-solid tumors and lymphomas. It is presently believed that any neoplastic cell can be treated using the methods described herein.

Tumor stem cells (also referred to as cancer stem cells (CSCs)) are considered to be the main drivers for the formation of metastases and the regrowth of tumors after resection.

In certain embodiments, compounds of the present invention are useful, inter alia, in the treatment of tumor stem cells in a subject.

In certain embodiments, compounds of the present invention are useful, inter alia, in the treatment of glioblastoma tumor stem cells in a subject.

In certain embodiments, the invention kills tumor cells and/or CSCs, or inhibits their growth, by oxidative stress, apoptosis and/or inhibiting growth of new blood vessels at the tumor site (anti-angiogenesis and anti-tubulogenesis). A primary mechanism of action for killing tumor cells and/or CSCs is oxidative stress. Tumor cells and/or CSCs may also be killed by apoptosis according to the invention. At lower blood concentrations, compounds according to the invention are effective at inhibiting tumor cell growth by their anti-angiogenic action and their anti-tubulogenic action, and these compounds are thus useful for palliative treatment.

Oxathiazin-like compounds and derivatives thereof of the invention metabolize much slower in the bloodstream than taurolidine and taurultam. Accordingly, lower doses of such compounds can be administered to a patient to achieve similar effects.

It was unexpectedly found that within minutes of exposure to taurolidine, tumor cells react by initiating the program of apoptotic cell death as follows:

1. The primary insult of Taurolidine to the tumor cell is an increase of reactive oxygen species (ROS), which is measured fluorimetrically.
2. The induction of oxidative stress by Taurolidine as the primary step is supported by the finding that the anti-neoplastic action of Taurolidine can be prevented by the addition of a reducing agent such as glutathione or N-acetylcysteine.
3. The damage caused by the elevated ROS to the mitochondria of the tumor cell results in the loss of their membrane potential and the release of Apoptosis Inducing Factor (AIF).
4. AIF is translocated to the nucleus and initiates the expression of pro-apoptotic genes, which results in the blebbing of the plasma membrane, in chromatin condensation and DNA fragmentation, the hallmarks of apoptosis.
5. In contrast to normal cells, tumor cells are very sensitive to oxidative stress. This explains the action of Taurolidine against a broad range of tumor cells, sparing normal cells.

Compounds of the present invention also are useful, in certain embodiments, in treatment of microbial infections in a subject, such as a human patient. Microbial infections which may be treated according certain embodiments include bacterial infections, fungal infections and/or viral infections.

Cancer patients tend to be immunocompromised, making them particularly susceptible to microbial infections, especially during and/or after surgery.

In certain embodiments, compounds of the invention are utilized to treat glioblastoma in a subject.

In certain embodiments, compounds of the invention are utilized to treat *S. aureus* infection in a subject.

In certain embodiments, compounds of the invention are utilized according to the invention to treat MRSA in a subject.

In certain embodiments, compounds of the invention are utilized according to the invention to treat *E. coli* in a subject.

In certain embodiments, compounds of the invention are utilized according to the invention to treat *H. pylori* in a subject, and/or cancer(s) associated with *H. pylori* in a subject.

In certain embodiments, compounds of the invention are utilized according to the invention to treat HIV in a subject.

In certain embodiments, compounds according to formula I are utilized according to the invention wherein R is H, alkyl, or the like, such as methyl, ethyl, propyl, (e.g., isopropyl), benzyl or the like.

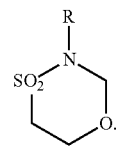

Formula I

Figure 8:
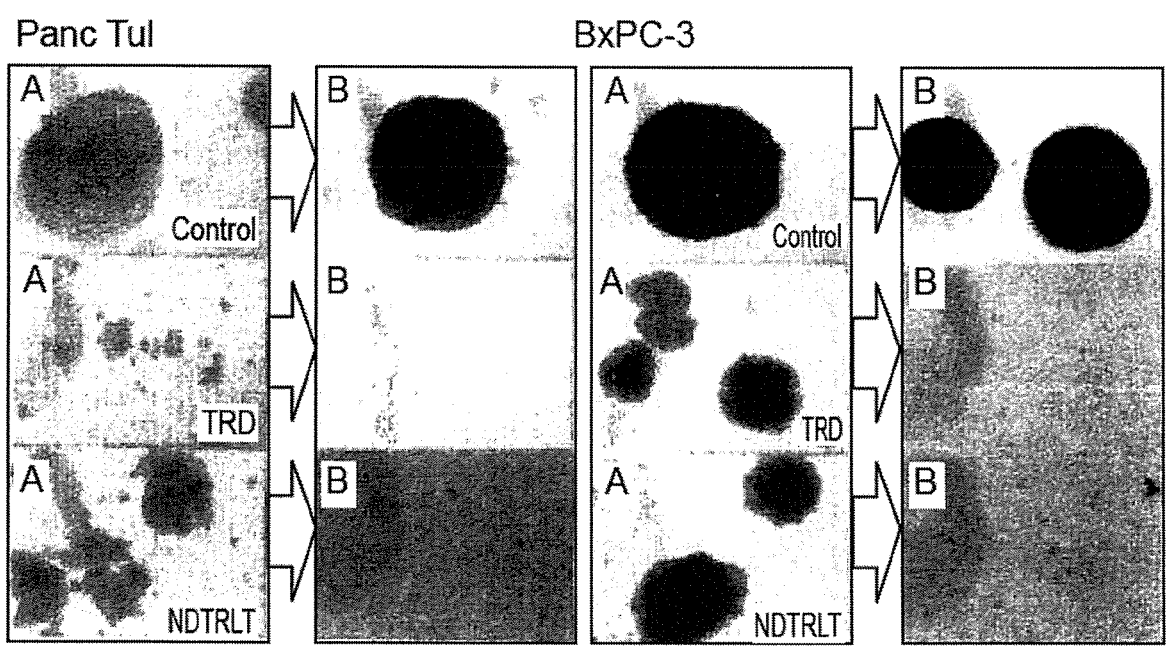
FIG. 8 shows the results of a spheroid toxicity assay for multicellular pancreatic tumor (Panc Tu1 or BxPC-3) spheroids in which control, taurolidine-treated (500 µM) or compound 2250-treated (1000 µM) samples were treated for 48 hours (columns labeled A) and strained to test residual aggregates (columns labeled B) for stability.

In certain embodiments, new compound 2250 (Tetrahydro1,4,5-oxathiazin-4-dioxide or 1,4,5-oxathiazan-4-dioxide) is prepared and/or utilized according to the invention. An FTIR spectrum for compound 2250 made according to the present invention is shown in FIG. 8.

In certain embodiments, new compound 2245 is prepared and/or utilized according to the invention.

Compound 2250 prevents and treats stomach tumors, including tumors caused by or associated with *H. pylori*, or tumors as a consequence of metastasis to the stomach.

The amount of the compounds needed depends on tumor size. In one embodiment, the invention includes surgically reducing tumor size and treating with one or more of the compounds. The compound may be administered before, during or after surgery to reduce tumors. Compounds according to the invention can be administered by any suitable method, including without limitation, by gels, capsules, tablets, IV, IP and/or directly to the tumor.

Gels can contain for example 2-4% (e.g., 3%) active compound of the invention, such as compound 2250, alone or in combination with taurolidine/taurultam which also can be administered and present alone, and can be for topical administration. Such gels can be used to treat tumors of the skin and mouth, including squamous cell tumors of the mouth and skin. Such gels also can be used to treat cervical cancer or cervical dysplasia by being administered in a suppository to the vagina, or by syringe. The invention may include the combination of a suppository carrying an active compound.

Solid dosage forms for oral administration include capsules, tablets, pills, powders, and granules. In such solid dosage forms, the provided composition is mixed with at least one inert, pharmaceutically acceptable excipient and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

The compounds of this disclosure, particularly compound 2250, have been found to be very soluble in water. In certain embodiments, no PVP necessary to increase the solubility. For example, a 3.2% solution 2250 is isotonic. This is an unexpected advantage over taurolidine.

Compounds of the invention, such as compound 2250 (with or without taurolidine and/or taurultam) are particularly useful in surgical oncology, since the compounds do not hinder wound healing. Administration of other antineoplastic drugs must be delayed for up to five weeks or more after surgery because other such antineoplastic drugs hinder wound healing and promote anastomotic leakage. Such problems can be avoided with compounds of the invention such as compound 2250, which can be administered during surgery and immediately thereafter, without wound healing issues or leakage issues.

Solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the provided composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

In certain embodiments, capsules may contain an excipient formulation containing one or more of hydroxypropyl methylcellulose (HPMC), gelatin, and fish gelatin. In certain embodiments, a capsule may contain compound 2250 in combination with taurolidine and/or taurultam. The capsule may optionally further contain one or more of lycopene, ellagic acid (polyphenol), curcumin, piperine, delphinidin, resveratrol, isothiocyanates such as sulforaphane, capsaicin, and piperlongumine.

Active compounds of the invention, such as compound 2250, can be combined with compounds such as gemcitabine. This combination can be used to treat cancers, such as pancreatic cancer. Taurolidine and/or taurultam also can be combined with gemcitabine to treat, for example, pancreatic cancer.

In some embodiments, a nutritional cancer prophylaxis and treatment product may contain 100-500 mg compound 2250 alone or in combination with 100-500 mg taurolidine and/or taurultam and one or more of lycopene, e.g., 20-200 mg, ellagic acid (polyphenol), curcumin, piperine (20-200 mg), delphinidin, resveratrol, isothiocyanates such as sulforaphane, capsaicin, and piperlongumine.

It was unexpectedly found that the compounds could be administered during surgery and immediately after surgery because the compounds do not inhibit wound healing like other chemotherapy agents.

It was unexpectedly found that taurolidine, taurultam, and oxathiazin-like compounds and derivatives thereof kill tumor stem cells, which is very unusual and perhaps unknown among chemotherapy agents. Typical chemotherapy agents, if effective against tumor stem cells, generally are only effective at very high doses which are extremely toxic to human patients.

It was unexpectedly found that lower doses of taurolidine and/or taurultam killed tumor stem cells than were needed to kill tumor cells.

It was unexpectedly found that Oxathiazin-like compounds and derivatives thereof have a half-life in human blood that is significantly longer than the half-life of taurolidine and taurultam. Accordingly, these compounds are cleared less rapidly from the bloodstream of the patients, thereby effectively delaying loss of drug potency caused by the body's clearance mechanisms.

It was unexpectedly found that certain Oxathiazin-like compounds and derivatives thereof have reduced burning sensation when applied directly into tissue, unlike this effect observed in patients treated with taurolidine.

It was unexpectedly found that the Oxathiazin-like compounds and derivatives thereof have a particularly advantageous combination of properties including high water solubility, versatile administration routes including oral and i.v., extended stability and half-life, and reduced side effect of burning sensation.

Thus, the half-life of compound 2250 is greater than 24 hours in human blood, which is significantly higher than the half-life of taurolidine, which was found to be ~30 minutes using the same test.

In one embodiment, the invention includes treating a patient by administering compound 2250 to the patient that results in a baseline blood concentration of compound 2250 within about 5 minutes of administration. The method involves maintaining a blood concentration of compound 2250 in the patient that is about 80% of the baseline blood concentration for about 20 hours.

In one embodiment, the invention includes maintaining a blood concentration of an anti-neoplastic compound in a patient that is about 80% of the patient's baseline blood concentration for about 20 hours by administering a daily dosage of compound 2250 once daily to maintain the blood concentration that is 80% of the baseline blood concentration.

The daily dosage may be about 0.1 g to about 100 g, e.g., about 5 g to about 30 g. The daily dosage may be administered in the form of an orally administrable composition. The daily dosage may be administered in the form of a capsule, a tablet, or a pharmaceutically acceptable solution. The daily dosage may be administered in a form that contains compound 2250 at a concentration of about 0.01 to about 3% w/v. The daily dosage may be administered in a form that contains compound 2250 at a concentration of about 0.01 µg/ml to about 1000 µg/ml. The daily dosage may be administered in a form that contains one or more solubilizing agents, e.g., polyols.

In some embodiments, the compounds are administered in compositions at a concentration of about 0.01 to about 1000 µg/ml. In some embodiments, the compounds are administered in compositions at a concentration of about 1 to about 100 µg/ml. In some embodiments, the compounds are administered in compositions at a concentration of about 10 to about 50 µg g/ml. The composition may also contain about 0.01 to about 1000 µg/ml, about 1 to about 100 µg/ml, or about 10 to about 50 µg g/ml taurolidine and/or taurultam.

In some embodiments, the compounds are administered in compositions at a concentration of about 0.01 to about 3%. In some embodiments, the compounds are administered in compositions at a concentration of about 0.1 to about 2.5%. In some embodiments, the compounds are administered in compositions at a concentration of about 1% to about 2%. The composition may additionally contain about 0.01 to about 3%, about 0.1 to about 2.5%, or about 1 to about 2% taurolidine and/or taurultam.

In one embodiment, the oxathiazin-like compounds and derivatives thereof may be administered as a co-therapy with taurolidine and/or taurultam to kill tumor stem cells. In accordance with such an embodiment, the co-therapy has been unexpectedly found to require a lower dosage of drug to kill tumor stem cells than necessary to kill normal tumor cells.

In certain embodiments, the oxathiazin-like compounds and derivatives thereof may be administered with Vitamin D3, which results to increase the anti-tumor effects of the compounds.

In one embodiment, the compound is administered to the subject at a total daily dose of from about 0.1 g to about 100 g, about 1 g to about 80 g, about 2 g to about 50 g, or about 5 g to about 30 g.

Effective dosage amounts of the compounds are dosage units within the range of about 0.1-1,000 mg/kg, preferably 150-450 mg/kg per day, and most preferably 300-450 mg/kg per day.

As used herein, the term pure refers to a substance that is at least about 80% pure of impurities and contaminants. In some embodiments, the term pure refers to a substance that is at least about 90% pure of impurities and contaminants. In certain embodiments, the term pure refers to a substance that is at least about 95% pure of impurities and contaminants. In some embodiments, the term pure refers to a substance that is at least about 99% pure of impurities and contaminants. In some embodiments, the term pure refers to a substance that is at least about 99.5% pure of impurities and contaminants.

In certain embodiments, compounds, compositions, and methods of the present invention encompass the use of micronized compounds. In some embodiments, the term "micronized" as used herein refers to a particle size in the range of about 0.005 to 100 microns. In certain embodiments, the term "micronized" as used herein refers to a particle size in the range of about 0.5 to 50 microns. In certain embodiments, the term "micronized" as used herein refers to a particle size in the range of about 1 to 25 microns. For example, the size of the drug particles may be about 1, 5, 10, 15, 20, or 25 microns.

In certain embodiments, compounds, compositions, and methods of the present invention encompass the use of nanoparticles. As used herein, the term "nanoparticle" refers to any particle having a diameter of less than 1000 nanometers (nm). In some embodiments, a nanoparticle has a diameter of less than 300 nm. In some embodiments, a nanoparticle has a diameter of less than 100 nm. In some embodiments, a nanoparticle has a diameter of less than 50 nm, e.g., between about 1 nm and 50 nm. Suitable formulations for injection or infusion may comprise an isotonic solution containing one or more solubilizing agents, e.g., polyols such as glucose, in order to provide solutions of increased compound concentration. Such solutions are described in EP 253662B1. The solution can be rendered isotonic with ringer solution or ringer lactate solution. The concentration of the compound in such solutions may be in the range 1-60 g/liter.

In certain embodiments, exemplary compounds and processes for making compounds of the invention include the following:

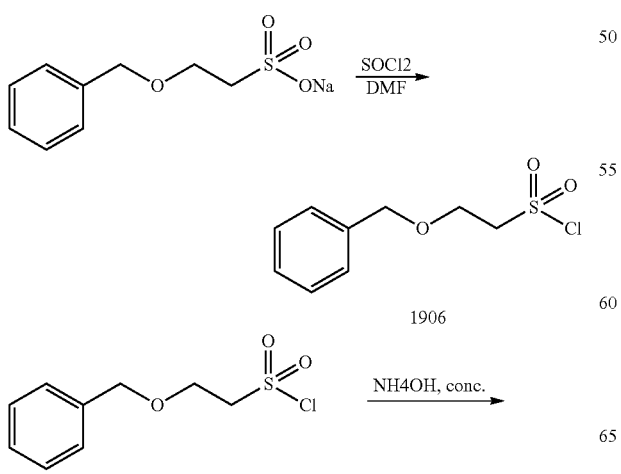

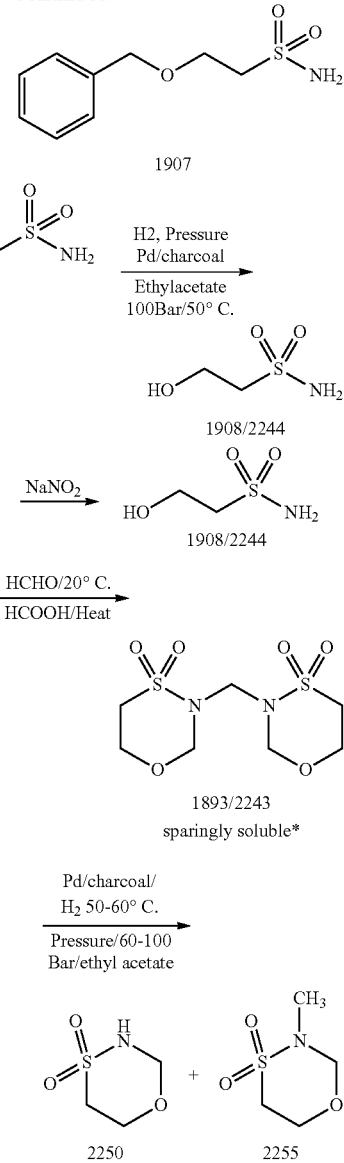

The compounds may be in crystalline form, e.g., after crystallization and/or recrystallization in an alcohol, ketone, ester, or combination thereof. For example, the compounds of the present invention may be crystallized and/or recrystallized from an alcohol such as ethanol.

Exemplary compounds of the invention include the following:

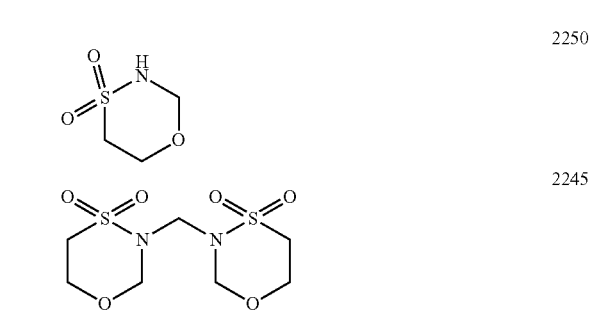

-continued

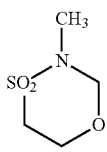
2255

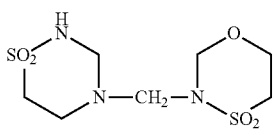
B1

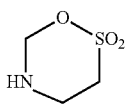
A1

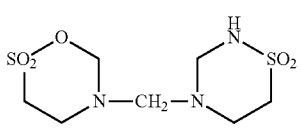
B2

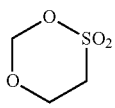
A3

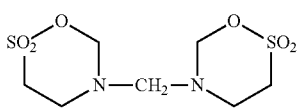
B3

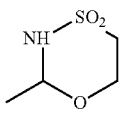
B4

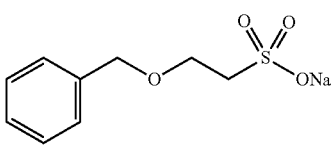
2256

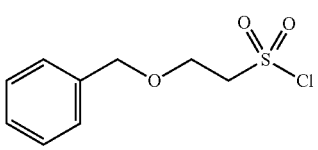
1906

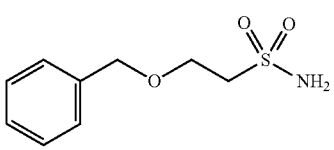
1907

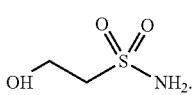
1908

It has been found that when used in the form of nanoparticles, the compounds of the claimed invention achieve higher blood levels. In one embodiment, the present invention includes compound 2250 alone or in combination with taurolidine and/or taurultam. For example, the present invention includes nanoparticles of the compounds of the present invention encapsulated in capsules.

In certain embodiments, the invention also relates to derivatives of the above compounds having, e.g., activity as described herein of said compounds, for example, at least 25%, 30%, 40%, 50%, 60%, 70%, 80%, 90%, 95%, 100%, or more, of said activity.

In certain embodiments, the invention also relates to compositions containing the compounds described herein, including pharmaceutically acceptable solutions of said compounds, as well as orally administrable compositions such as capsules and tablets containing said compositions.

In certain embodiments, the compounds of the present invention can be administered to a subject or patient by any suitable means, for example, in solution, e.g., locally, systemically such as by intravenous infusion, or the like.

Synthesis of 2250

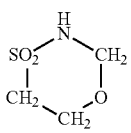
2250 sublimes in a vacuum at ~70-80° C.
Starting materials:
Isethionic Acid,
Carbylsulfat, Taurin, Taurinamide,
Cysteine, Isethionic Acid, inter alia
Synthesis 1
I.

a. Isethionic Acid via Carbylsulfate

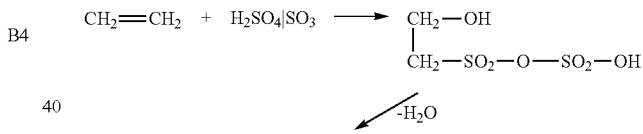

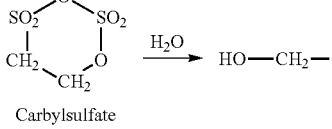

Carbylsulfate
b. Isethionic Acid via Taurin
Biochemical synthesis via Cysteine, Taurin

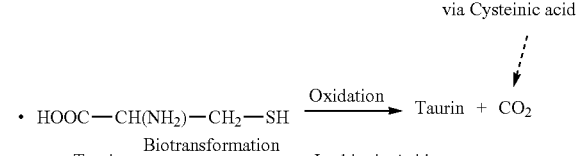

Chemical Synthesis
ethylenoxide with bisulfite
II. Isethionic Amide

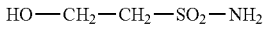

a.

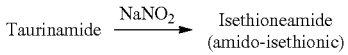

11
-continued
NH₂—CH₂—CH₂—SO₂NH₂ ⟶
[O=N—NH—CH₂—CH₂—SO₂NH₂]
↓
HO—CH₂—CH₂—SO₂—NH₂ + N₂
b.
Carbylsulfate + NH₃
12
-continued
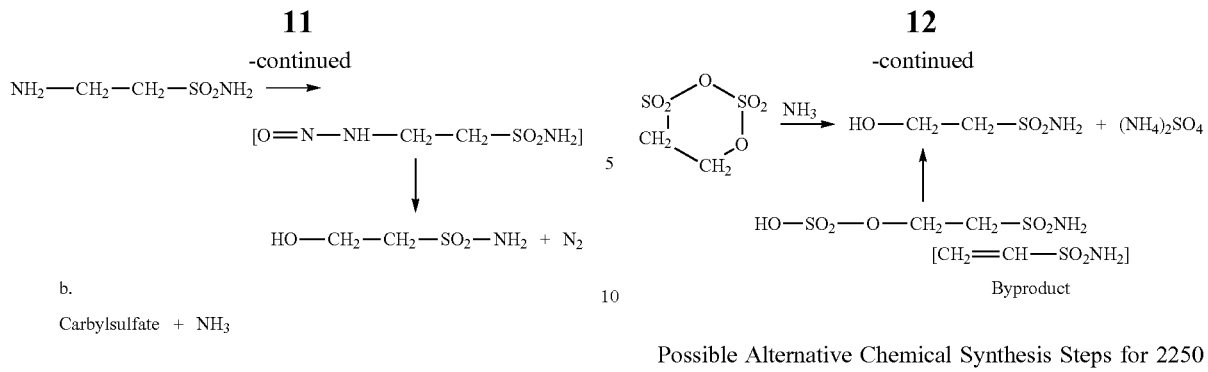
[CH₂=CH—SO₂NH₂]
Byproduct
Possible Alternative Chemical Synthesis Steps for 2250
a) Sulfamic acid
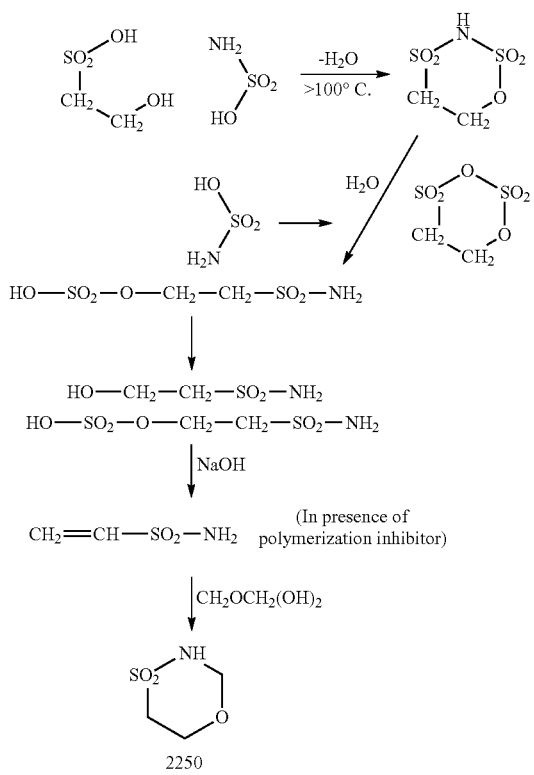
b) Paraformaldehyde, Hexamethylenetetramine
(Hexamine, Formine, Urotropin)
c)
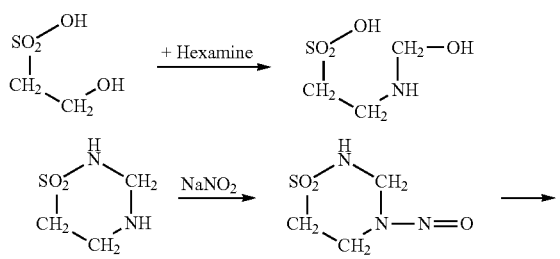

-continued
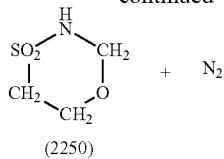
(2250) + N$_2$
d)
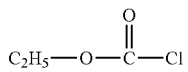
or
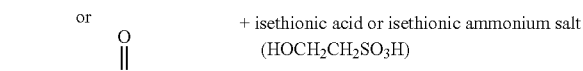
+ isethionic acid or isethionic ammonium salt
(HOCH$_2$CH$_2$SO$_3$H)
↓ DMF
C$_2$H$_5$—O—C(=O)—O—CH$_2$—CH$_2$—SO$_3$H or CH$_3$—O—C(=O)—O—CH$_2$—CH$_2$—SO$_3$H
↓ SOCl$_2$/DMF
C$_2$H$_5$—O—C(=O)—O—CH$_2$—CH$_2$—SO$_2$—Cl
or
CH$_3$—O—C(=O)—O—CH$_2$—CH$_2$—SO$_2$—Cl
↓ NH$_3$
C$_2$H$_5$—O—C(=O)—O—CH$_2$—CH$_2$—SO$_2$—NH$_2$
or
CH$_3$—O—C(=O)—O—CH$_2$—CH$_2$—SO$_2$—NH$_2$
e)
1) 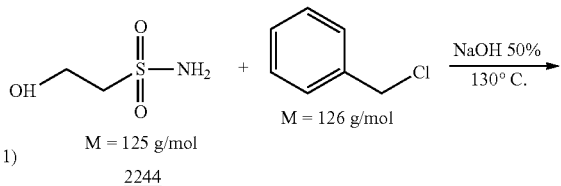
M = 125 g/mol
2244
M = 126 g/mol
NaOH 50%
130° C.
→
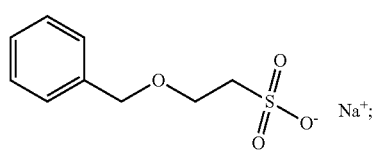
M = 238 g/mol
2260
2) 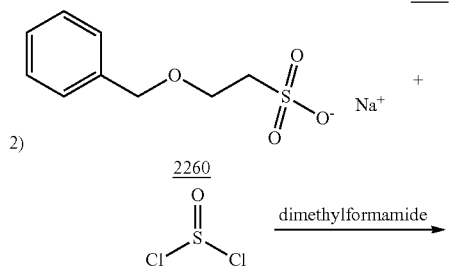
2260
+
O=S(Cl)(Cl)
dimethylformamide
→

-continued
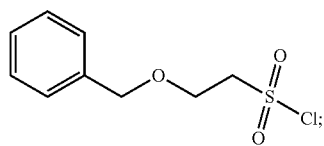
2261
3) 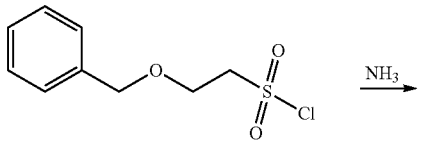
2261
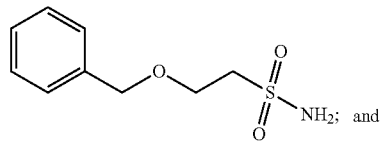
2264/1907; and
4) 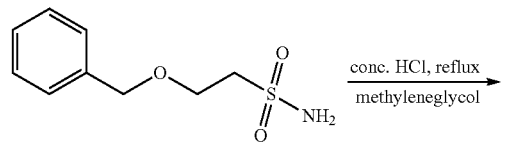
2264/1907
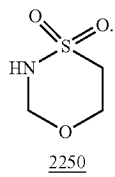
2250
f)
1) 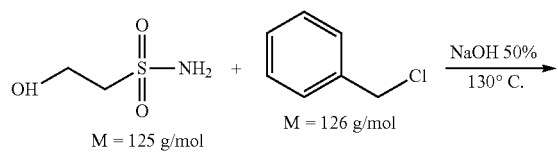
2244
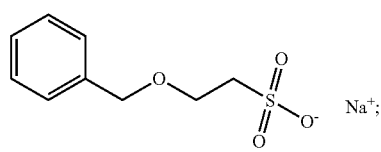
2260
2) 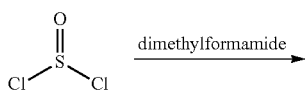
2260

-continued
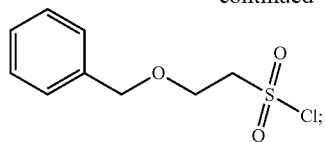
2261
3) 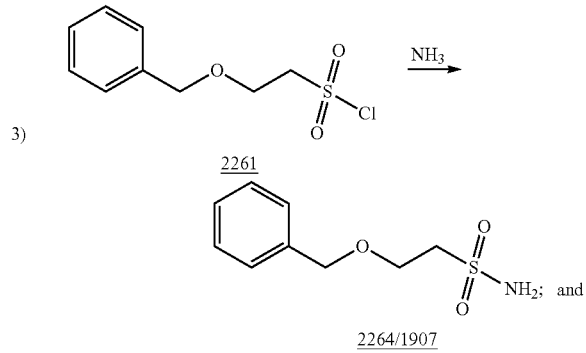
4) 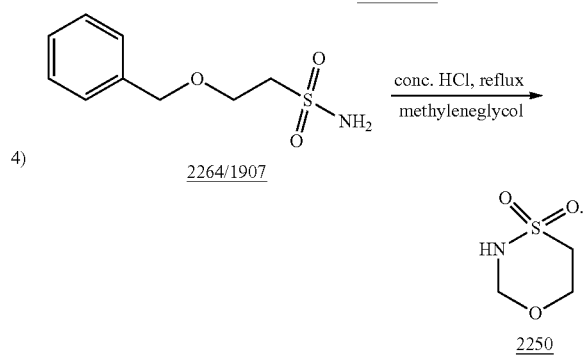
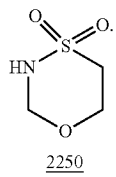
2250
g)
1) 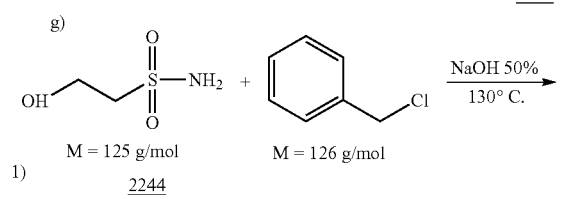
2) 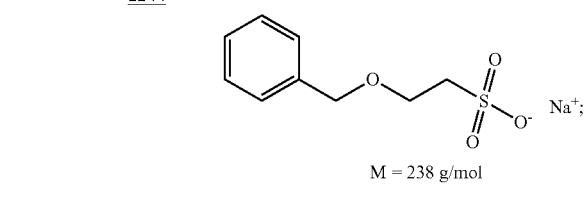
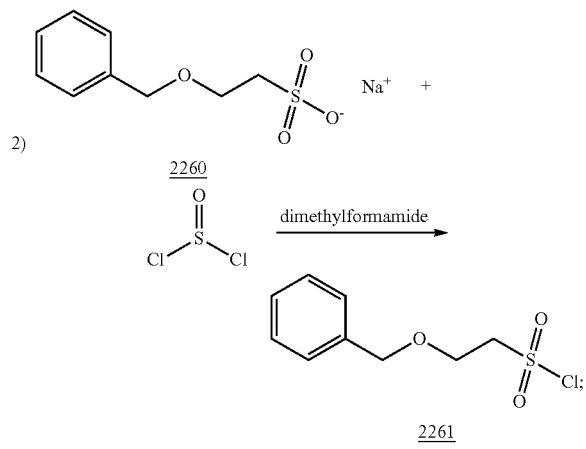
2261

-continued
3)
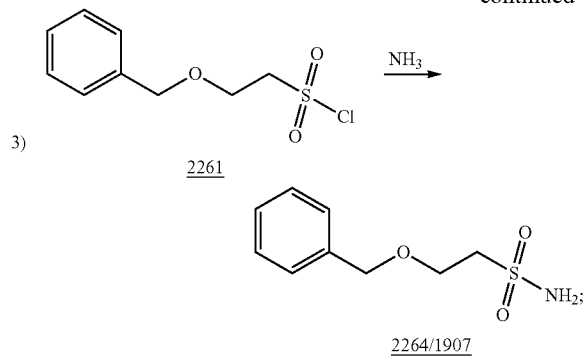
4)
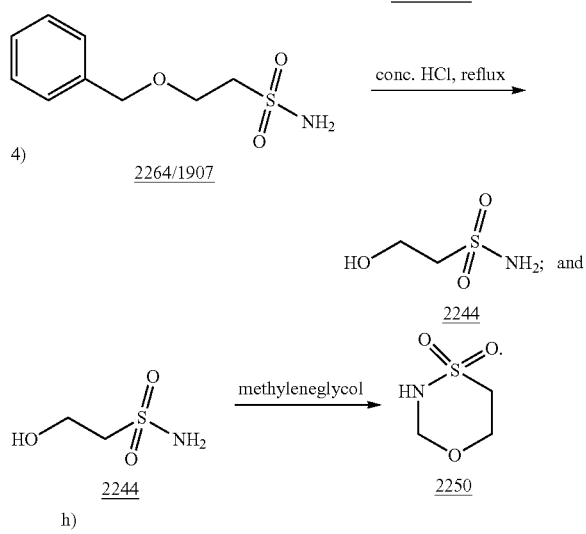
h)
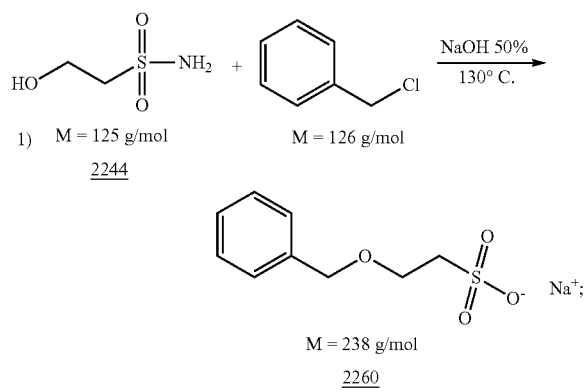
1)
2)
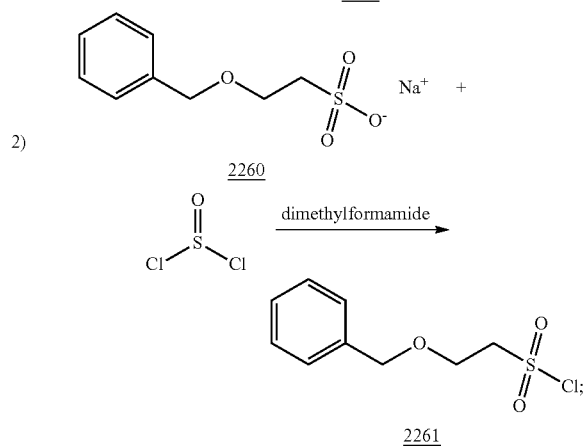

3)
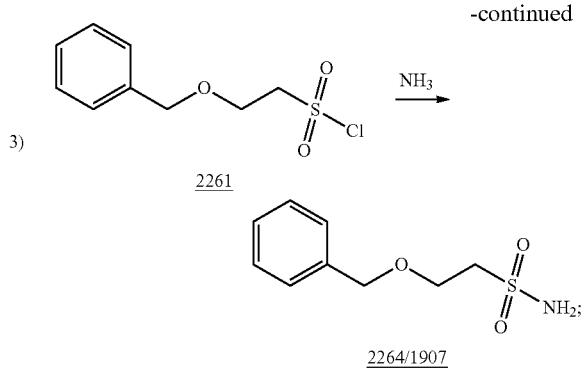
4)
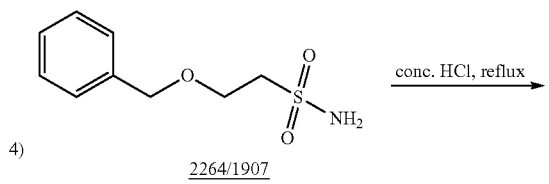
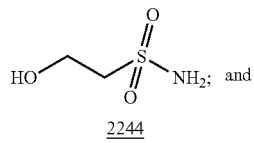
5)
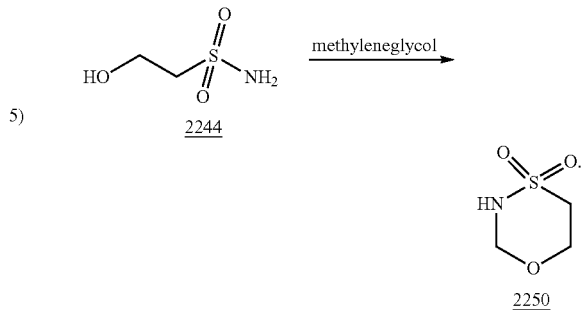
Several Alternative Synthesis Steps for 2250 and 2255
I. Starting Materials 2250/2255
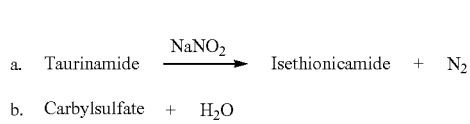
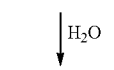
Isethionic acid
Synthesis sodiumisethionate from Ethylenoxide+Sodium-hydrogensulfite
II. Reaction of Amine with Carbylsulfate
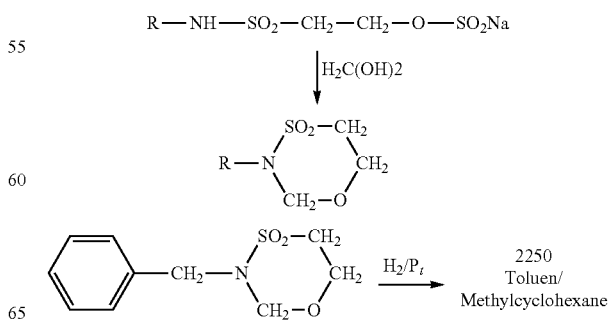

-continued

2250 → +CH₂(OH)₂/HCOOH

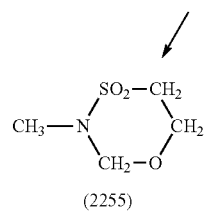

(2255)

III.
Exemplary Synthetic Protocols
 I. Synthesis of 2244

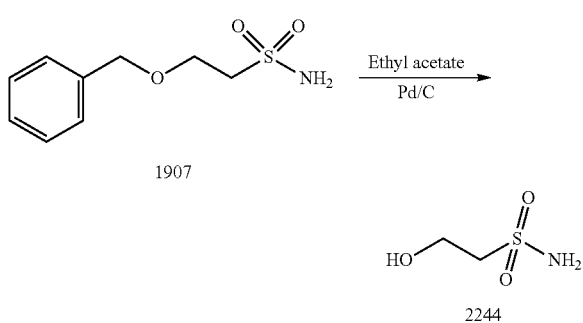

2.15 g of pure 1907 was dissolved in 100 ml acetic acid ethyl ester, and catalyzed using 0.5 g palladium on activated carbon. The solution was hydrogenated at room temperature and atmospheric pressure. The hydrogenation was complete after about 15 hours and the absorbed amount of hydrogen was 450 ml.

The hydrogenation was evacuated 3 times, each time with nitrogen, and then the reaction mixture was filtered through a filter aid (diatomaceous earth). The clear colorless ethyl acetate solution was concentrated and dried in a rotary evaporator.

Yield: 1.25 g, which was innoculated with crystalized 2244.
Melting point: 42-44° C.
IR: corresponds to 2244, 99.3% pure.
 II. Synthesis of 2244

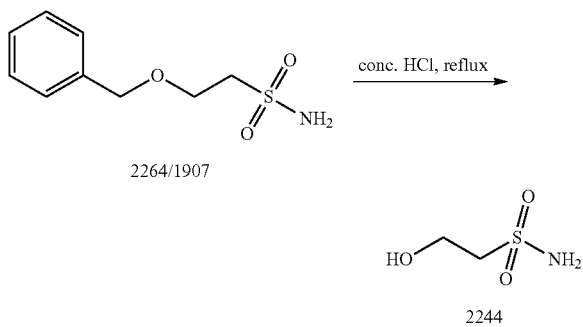

5 g (0.023 mol) of 2264/1907 was boiled in 50 ml of concentrated HCl for 3 hours under reflux, then allowed to cool to room temperature and separated with 30 ml of dichloromethane in a separating funnel. The aqueous phase was evaporated in a rotary evaporator and dried. A yellow oil remains which slowly crystallized after seeding with 2244 crystals.

IR corresponds to the substance 2244.
Recrystallized from ethyl acetate.
0.7 g obtained (24%).
Melting point: 44-45° C.
IR corresponds to the reference substance.
 III. Synthesis of 2244

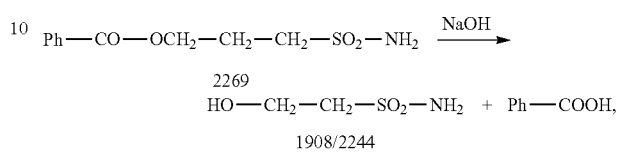

wherein Ph is a phenyl group.

230 mg 2269 was dissolved in 2 ml NaOH (1N) and refluxed at boiling with a reflux condenser for 15 minutes. The clear solution was cooled to 20° C. and acidified with hydrochloric acid. The resulting precipitate was filtered off under vacuum and dried.

Yield: 110 mg.
Melting point: 114-116° C.
IR showed 99% benzoic acid as by-product.
The acidic solution was concentrated to dry it on a rotary evaporator and the solid was boiled with acetic ester. The ethyl acetate solution was filtered and concentrated to dryness under vacuum.

Weight: 110 mg. Oil was contaminated with oil and the IR peak for 2244 (isethionic acid amide) was unclean.
The 110 mg was recrystallized from acetic ester.
Yield: 65 mg, Melting Point: 43-45° C.
IR corresponded to 52% 2244.
 IV. Synthesis of 2244

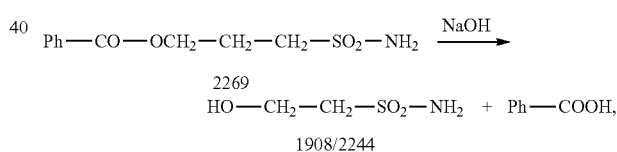

wherein Ph is a phenyl group.

1.15 g 2269 was dissolved in 10 ml NaOH (1 N) and refluxed at boiling for 15 minutes. The clear solution was cooled to 20° C. and acidified with hydrochloric acid. The resulting precipitate was filtered off under vacuum and dried.

Yield: 0.5 mg.
Melting point: 114-116° C.
IR showed 82% benzoic acid by-product as control substance. Hydrolysis is not complete.
The acidic solution was concentrated to dry it on a rotary evaporator and the solid was boiled with acetic ester. The ethyl acetate solution was filtered and concentrated to dryness under vacuum.

Weight: 0.8 g. Oil was contaminated with oil and the IR peak for 2244 (isethionic acid amide) was unclean.
The 0.8 g was recrystallized from acetic ester.
Yield: 160 mg, Melting Point: 43-45° C.
IR corresponded to 26% 2244.

V. Synthesis of 2244

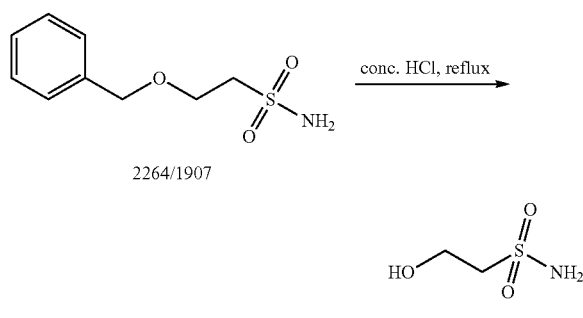

2264/1907

2244

Figure 7:
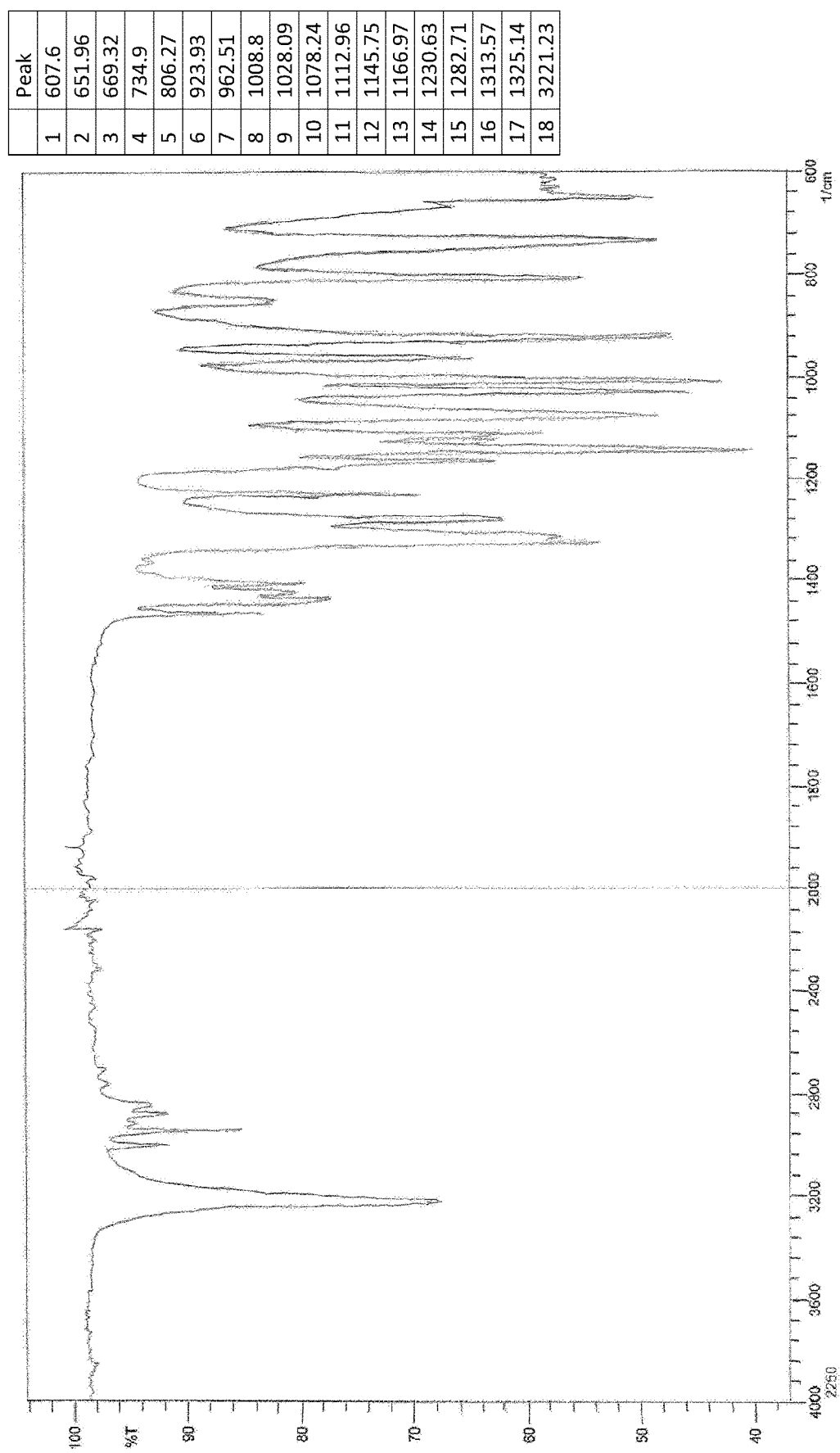
FIG. 7 FTIR spectrum of compound 2250 made according to the present invention.

215 g 0.1 Mol 2264 and 1000 ml of concentrated hydrochloric acid (ca. 36%) were boiled together for 30 minutes under reflux. The 2264 resolved and there was an oily layer. The reaction mixture was allowed to cool and transferred to a separatory funnel where the oil was separated from the water phase. The acidic aqueous solution in which should be solved isethionic acid amide (2244) was concentrated at 50° C. in a rotary evaporator almost to dryness. The yellow oily residue was placed overnight in the refrigerator and 32.3 g of clear crystals were filtered off under vacuum. Mp 43-45° C. IR: in oxygen having peaks at the following wave numbers 655.82, 729.12, 844.85, 898.86, 947.08, 1003.02, 1060.88, 1134.18, 1236.41, 1288.49, 1317.43, 1408.08, 1572.04, 3105.5, 3209.66, 3313.82, and 3427.62 cm$^{-1}$ as shown in FIG. 7. The mother liquor was concentrated to complete dryness.

VI. Synthesis of 2244

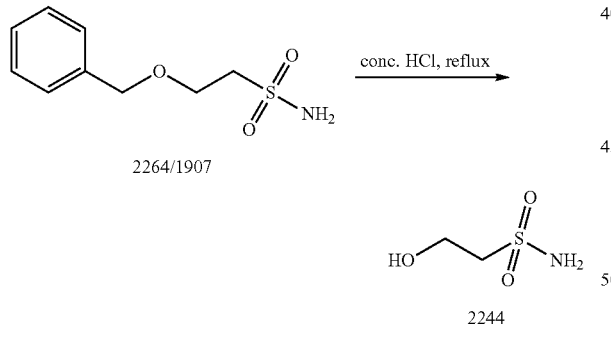

2264/1907

2244

21.5 g 0.1 Mol 2264 and 100 ml of concentrated hydrochloric acid (ca. 36%) were boiled together for 30 minutes under reflux. An oily layer formed and the reaction mixture was allowed to cool in a separatory funnel where the oil was separated from the water phase. The acidic aqueous solution in which the isethionic acid amide (2244) was dissolved and shaken 2 times with methylene chloride, the methylene chloride was separated, and the acidic water solution was concentrated in a rotary evaporator at 50° C. to dryness. The yellow oily residue was placed overnight in the refrigerator and 12.3 g of oil was obtained. Mp.: 41-43° C. Analysis of the product showed that corresponds 99.8% to 2244 by IR.

Distillation Experiment:

12.3 g were distilled under high vacuum:

| Outside Temperature | Inside Temperature | Vacuum |
|---|---|---|
| 190-210° C. | 183-186° C. | 0.1 mm |

Weight: 9.3 g of oil which was solid at room Temperature Mp: 43-45° C.

VII. Synthesis of 2244

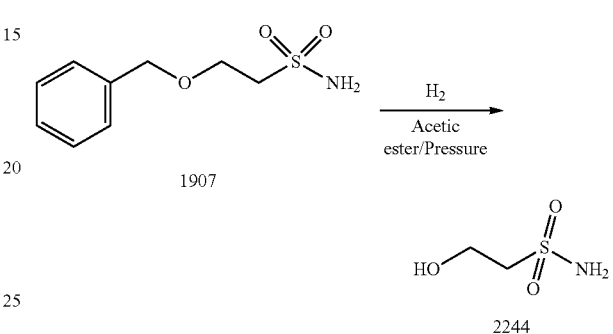

1907

2244

2.0 g of pure compound 1907 was dissolved in 200 ml acetic ester and 0.5 g palladium/activated carbon was added and the mixture was autoclaved at 100° C. and hydrogenated at 50° C. After 6 hours run-time, the reaction mixture was allowed to cool overnight, and was then filtered and concentrated to dryness under vacuum.

Wt.: 1.7 g oil—added CH2Cl2 and shaken, then allowed to stand—then suction filtered result in crystalline solid having Wt.: 0.6 g, melting point ca. 40° C.

For analysis 0.2 g of two-times acetic ester was added to crystallize. Melting point 43-44° C.

VIII. Synthesis of 2244

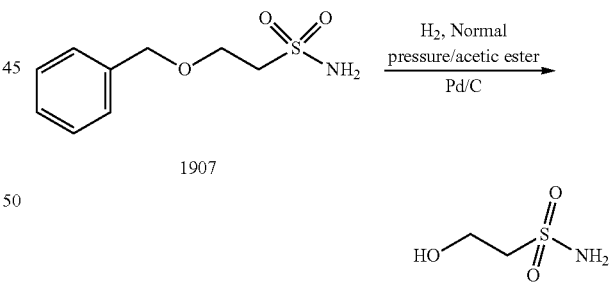

1907

2244

2.15 g of pure 1907 was dissolved in 100 ml acetic acid-ethyl ester, then added to 0.5 g palladium/activated carbon. Then the mixture was hydrogenated at room temperature and atmospheric pressure. Hydrogenation was terminated after approximately 15 hours. The absorbed amount of hydrogen was approximately 450 ml. The hydrogen was then evacuated 3 times and flushed with nitrogen, and then each reaction mixture was filtered through diatomaceous earth (celite). The clear, colorless solution, ethyl acetate was evaporated to dryness on a rotary evaporator.

Wt.: 1.25 g oil which crystallized after seeding with 2244 crystals.
Melting point: 42-44° C.
IR: corresponds to 99.3% 2244.

IX. Synthesis of 2250

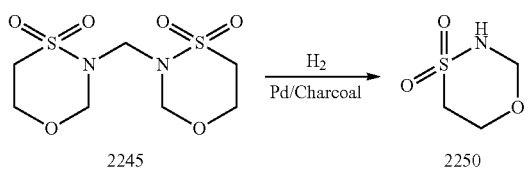 [SMILES: O=S1(=O)CCOCN1CN1COCCS1(=O)=O ; "H2" ; O=S1(=O)CCOCN1]

1.2 g pure 2245 pure was dissolved in 150 ml acetic acid purely solved at 60° C. 0.3 g of palladium on activated carbon was added and was stirred at 75° C. and the mixture was hydrogenated at atmospheric pressure.
Hydrogenation was stopped after 7 days. The absorbed amount of hydrogen was approximately 480 ml.
The hydrogen was evacuated and purged 3 times with nitrogen.
Then the reaction mixture was filtered at 70° C. through a filter aid (Diatomaceous earth).
The clear warm glacial acetic acid solution was cooled down to room temperature and white crystals were suction filtered.
Weight: 0.74 g, Melting Point: 225-227° C.
IR: 2245 corresponds to the starting material
The mother liquor was concentrated on a rotary evaporator to dryness.
Weight: 0.38 g of impure material was extracted with ethyl acetate.
The solution was concentrated.
Ethyl acetate Soluble Portion: Semi-solid substance obtained by sublimation;
Obtained 0.15 g semi-solid substance that was recrystallized from a few drops of water
Yield: 70 mg, Melting Point: 95-98° C.
IR corresponded to 98% 2250.

X. 1-step Synthesis in High Yield of Sodium 2-benzylether ethanesulfonate

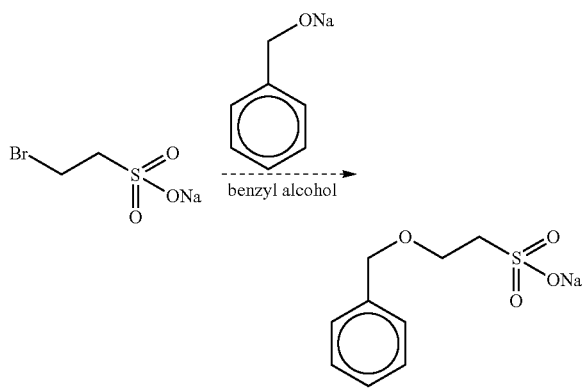

10.5 g sodium 2-bromoethanesulfonate was added to a solution of 110 ml benzyl alcohol and 1.15 g sodium benzyloxide.
Then the mixture was boiled under reflux four times. The mixture was then concentrated under vacuum to dryness and then boiled with ethyl alcohol three times. The alcohol was filtered and concentrated to dryness.
The yield was 9.8 g and was confirmed by UV and IR.
Pure crystals were obtained by boiling the resultant sodium 2-benzylether ethanesulfonate in ethyl alcohol, filtering, then cooling the solution to crystallize pure sodium 2-benzylether ethanesulfonate crystals out of solution.

XI. Synthesis of 2250

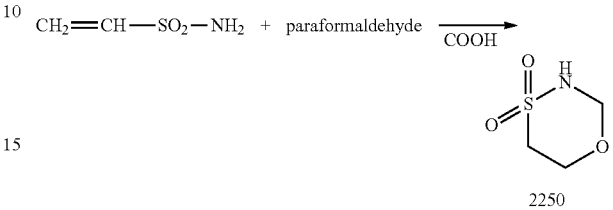

6.3 g vinylsulfonamide (from 2258),
50 ml of concentrated formic acid, and
1.1 g of paraformaldehyde were combined for 2 hours at reflux to produce compound 2250. Then, the clear acidic solution was concentrated on a rotary evaporator to dryness.
Residue is: 5.9 g of pale yellow, honey-like syrup.
IR: Mixture of vinylsulfonamide and 2250
A 2 grams was sublimated and a few crystals were obtained.
Sublimate semisolid: IR: corresponds to 98% 2250.

XII. Synthesis of Vinylsulfonamide

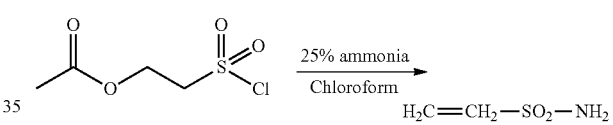

Formyl isethionic chloride was placed in 50 ml of chloroform and was placed in a 350 ml sulfonation flask and cooled to −10° C. Then 25% ammonia gas was introduced. After introduction of the ammonia gas, the weight of the chloroform/NH3 was found to be 5 g.
From −3° C. to 2° C., the mixture was stirred slowly.
To 9.0 g distilled 2249
20 ml of chloroform was added drop wise. NH$_4$Cl precipitated immediately.
Then the ammonium chloride was filtered off under vacuum and the clear chloroform solution was concentrated in a rotary evaporator until dry.
Yield: 6.3 g of clear, thin oil.
IR: corresponds to 96% CH2=CH—SO2-NH2 (vinylsulfonamide).

XIII. Synthesis of 2261

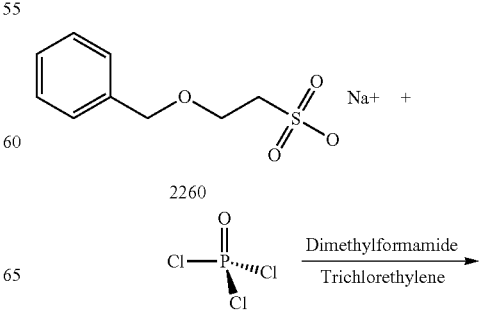

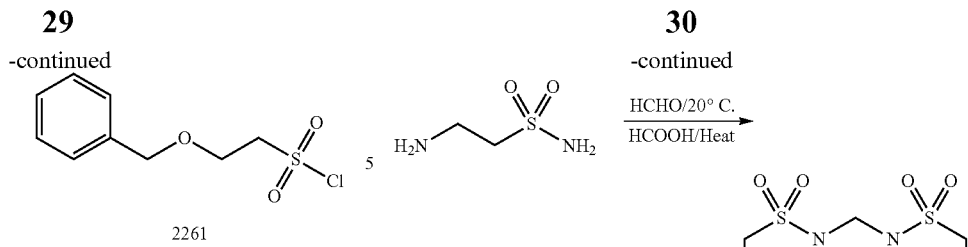

300 g (1.26 mol) 2260 was weighed into a 750 ml multi-necked flask with KPG-stirrer.
415 ml trichloroethylene+phosphorus oxychloride (Density corresponds to about 1.47 in 10% $POCl_3$) and
150 ml phosphorus oxychloride and 5.7 ml DMF was warmed to 105° C. while stirring.
The mixture was allowed to react for 5 hours.
The solid was filtered by vacuum and the liquid was distilled under water-pump vacuum. The filter cake was washed with ethyl acetate. After distilling off of trichloroethylene and phosphorus oxychloride, the wash-acetate was transferred into a flask and also distilled.
250 g (1.07 mol-85%) of a yellow liquid was collected. IR corresponds to 2261.

XIV. Synthesis of 2250 and 2255:

XV. New Synthesis schemes for compound 2250 and related compounds:

Starting materials:

3-Hydroxypropane-1-sulfonic acid

3-Hydroxy-propane-sulfonic acid-γ-sultone (1,3-Propane-sultone)

3-Hydroxy-propane-2-sulfonic acid

2-Hydroxy-propane-1-sulfonic acid

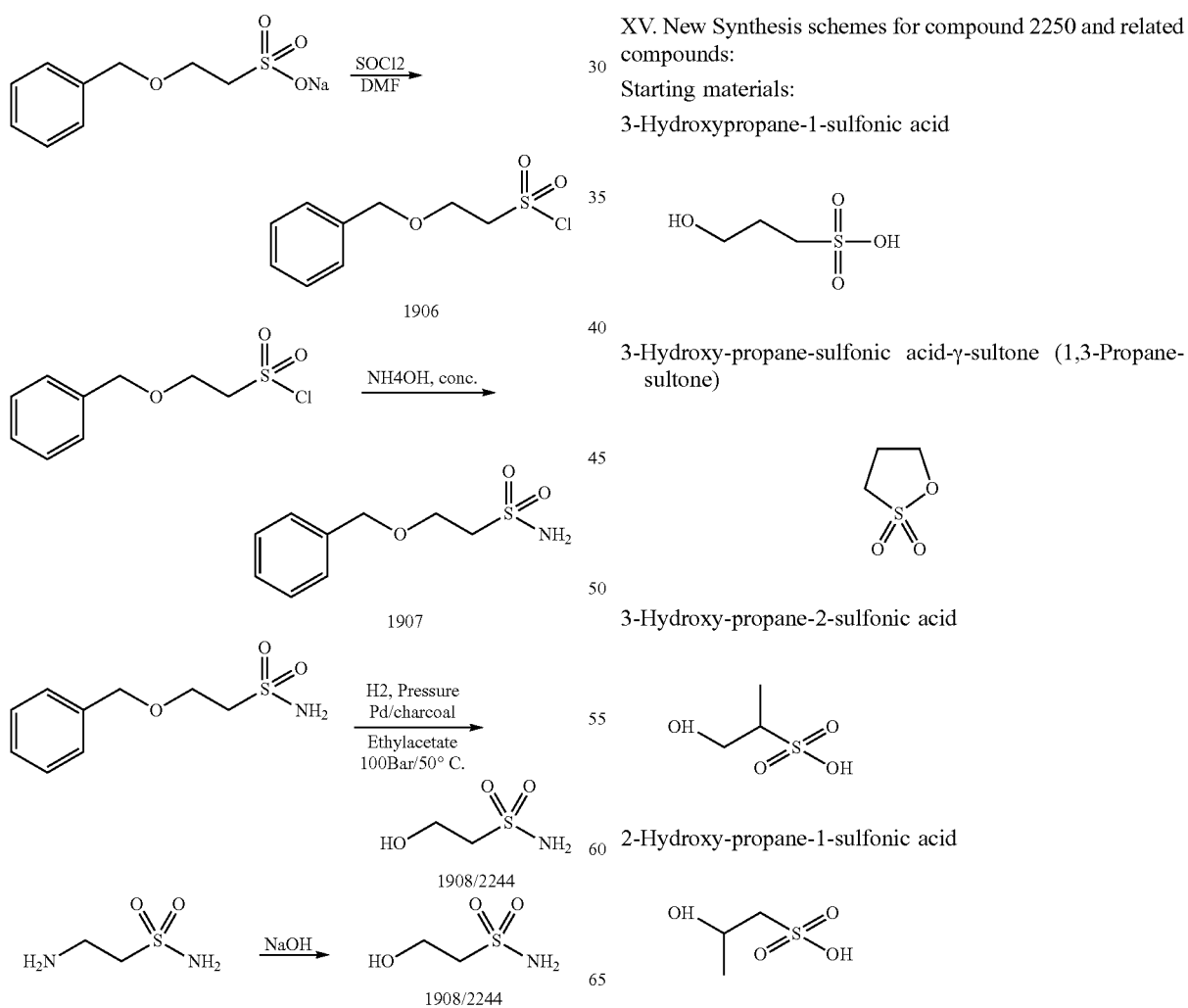

Compounds (Tetrahydro-oxathiazine-dioxide):

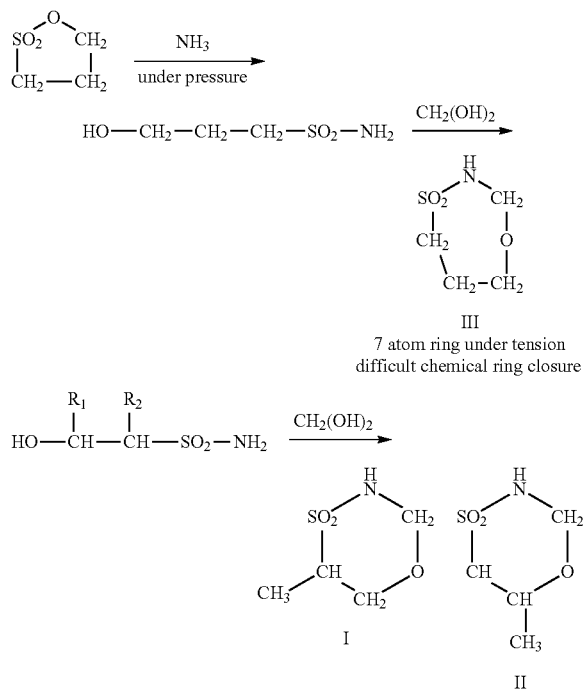

$R_1 = H, CH_3$
$R_2 = H, CH_3$

Chemical Intermediates
Protecting group: Benzyl chloride $R_1 = H, CH_3$
$R_2 = H, CH_3$ Protecting group: Benzyl chloroformate XVI. Synthesis of Precursor Compounds Synthesis:
83.9 g vinylsulphonic acid sodium was added to a solution of 400 ml benzylalcohol and 0.5 g sodium (catalytic amount) was added. The mixture was warmed with stirring to 150° C. and most of the vinylsulphonic acid sodium went into solution. After 3 hours, the mixture was allowed to cool overnight and a thick solid crystallized. This solid was vacuum-filtered and then suspended in ethyl alcohol, vacuum-filtered and dried.
Yield: 94.0 g, IR: corresponds to the desired compound (61.2% pure).

XVII. Synthesis of 1905

-continued

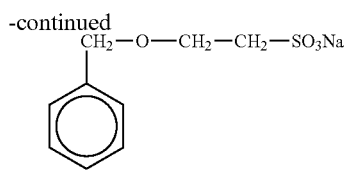

60 grams of vinylsulfonic acid sodium were added to a solution of 1000 ml benzylalcohol and 0.5 g of sodium. Then, the whole mixture was stirred under reflux and heated. After approximately 3 hours, the excess benzyl alcohol was distilled and removed by vacuum and the rest was boiled with alcohol. The alcohol solution was filtered, concentrated, crystallized to about ½, 37.3 g of a yellow cotton-wool-like substance was obtained.

The procedure was also repeated with 250 g vinylsulfonic acid sodium and 2 liters of benzyl alcohol, processed as above and about 208 g was crystallized.

The procedure was also repeated with 100 g vinylsulfonic acid sodium and 1 liter of benzyl alcohol, processed as above and about 105 g was crystallized.

The procedure was also repeated with 200 g vinylsulfonic acid sodium, processed as above and about 130 g was crystallized.

XVIII. Synthesis of 1906

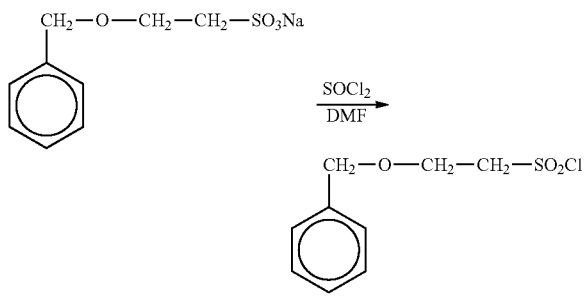

6.7 g of 1905 (recrystallized) was added to 50 ml thionyl chloride and 1 ml dimethyl formamide. The sodium salt dissolved immediately and the mixture was heated to 40-50° C., let stand overnight at 20° C. and vacuumed until concentrated. Yield: 9.8 g, which was added to 50 ml NaOH 2N and stirred well. The NaOH solution was washed with $CHCl_3$ and then shaken with concentrated HCl to precipitate and captured with $Na_2SO_4$, then dried and distilled.

The process was repeated with 208 g 1905 mixed with 1000 ml thionyl chloride and 10 ml dimethyl formamide. The mixture was refluxed and the excessive thionyl chloride was distilled off until dry. The yield was 250 g, which was processed as above.

XIX. Synthesis of 1907

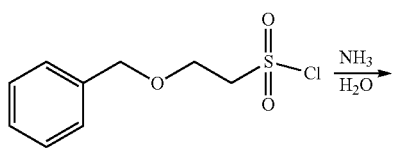

-continued

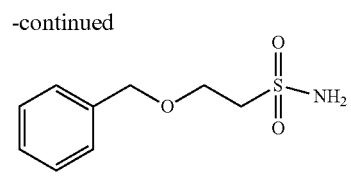

9.8 g of 1906 was dissolved in chloroform (CHCl3) (turbid) and concentrated into a portion of 150 ml concentrated ammonia in water and stirred. Stirring was continued for 3 hours with heating to 40-50° C. Then, the mixture was dried under vacuum and concentrated.

Yield: 3.1 g dark oil

The 3.1 g dark oil was added to 50 ml NaOH 2N and stirred well. The NaOH solution was washed with $CHCl_3$ and then shaken with concentrated HCl to precipitate and captured with $Na_2SO_4$, then dried and distilled. Yield: 2.5 g oil For analysis, a sample of 0.5 g was condensed at a temperature of 160° C., became solid and crystallized 3 times from ethyl acetate/benzene.

Melting point: 75-76° C.

Molecular formula: $C_9H_{13}NO_3S$

MW: 215.2

Calculated: C=50.23%, H=6.09%, N=6.51%, S=14.86%

Actual: C=50.14%, H=6.15%, N=6.35%, S=14.79%

XX. Synthesis of 1908

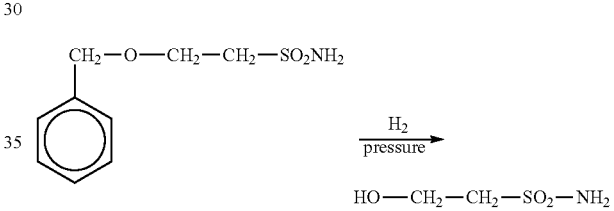

1.2 g of 1907 was dissolved in 200 ml ethyl acetate and 0.4 g Pd activated carbon was added. The mixture was hydrogenated in a hydrogenated autoclave at 100 and at 50° C. for 4 hours. The mixture was left under pressure for a weekend at room temperature. Then the ethyl acetate solution was filtered and dried under vacuum.

Yield: 1.1 g oil.

XXI. Synthesis of 1908

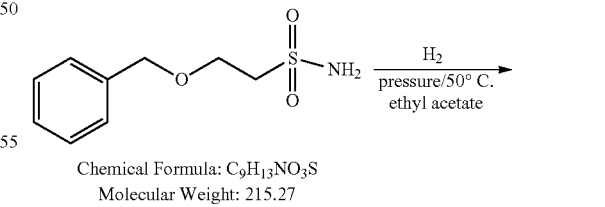

2 grams of 1907 were dissolved in 200 ml ethyl actetate and 0.5 g

Pd/Palladium/activated carbon was added. The mixture was hydrogenated in a high pressure autoclave at 100 and at 50° C. After 6 hours, the reaction mixture was left to cool overnight, then filtered and distilled under vacuum until it dried to a residual oil.

Yield: 1.7 g oil.

CH2Cl2 was added, agitated and allowed to stand, crystallized, and separated with suction under vacuum. Weight: 0.6 g, melting point about 40° C.

Analysis:

0.2 g recrystallized 2 times from ethyl actetate.

Melting point: 43-44° C.

Molecular formula: $C_2H_7NO_3S$

MW: 125

Calculated: C=19.22%, H=5.65%, N=11.21%, S=25.65%

Actual: C=19.20%, H=5.67%, N=11.07%, S=25.73%

XXII. Synthesis of 1909

19.9 grams of 1906 were dissolved in 100 ml chloroform and added into a solution of 23 grams pure benzylamine and 200 ml pure chloroform. Immediately, benzylamine hydrochloride precipitated and the reaction mixture became warm. The mixture was then refluxed and the hydrochloride compound was separated by suction and the clear CHCl3-mother liquor was put into vacuum for drying.

Yield: 27 g yellow clear oil that slowly became solid.

The 27 g was dissolved into about 20 ml ethyl acetate and N-hexane (q.s.) was added so that the solution became nearly turbid. The mixture was set aside in the cold overnight and it crystallized.

Yield: 9.2 g, melting point: 50-53° C.

For analysis, 1 g in N-hexane was recrystallized three times. Melting point 56-57° C.

XXIII. Synthesis of 2260

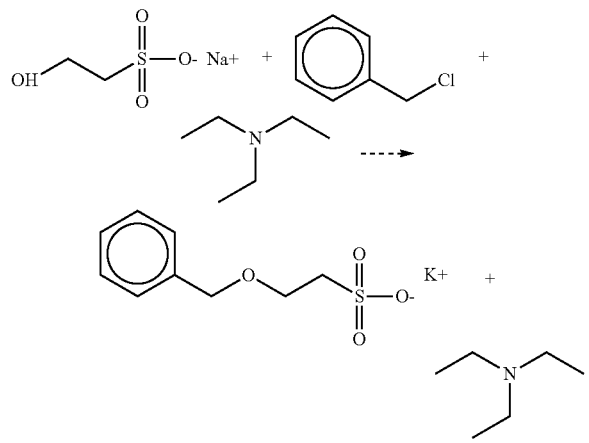

0.675 mol of isethionic acid sodium salt (100.0 g) and 2.02 mol benzylchloride (233 mL) were mixed in a 750 mL multi-necked flask with KPG-stirrer. The mixture was heated at 70° C. inside temperature (95° C. outside temperature) and then Triethylamine (120 mL) was added drop wise over one hour and the outside temperature was increased to 125° C. and maintained. Subsequently, outside temperature increased to 140° C., and the inside temperature rose to 130° C. A solid clustered at the stirrer, but went back into suspension. Hydrochloric acid vapors evolved.

30 mL of triethylamine was added drop wise and then reacted for 1.5 more hours. A viscous yellowish suspension formed. The product was allowed to cool to 50° C. inside temperature, then 300 mL water was added and vigorously stirred for 20 minutes and the mixture was transferred to a 2 L separatory funnel. Then, the flask was rinsed out with 100 mL of water.

The combined aqueous phases were washed twice with 280 mL dichloromethane.

The aqueous phase was held at 40° C., while KCl was added to the solution until saturated (about 130 g KCl). The mixture was filtered through a fluted filter and stored overnight in a refrigerator.

The remaining solid was extracted and dried, resulting in 30.85 g, yield of 17.9%.

IR: OH band is present, similar to the precursor.

The mother liquor was again treated with KCl and stored (at 35-40° C.) overnight in the refrigerator.

Solid from the second precipitation with KCl was filtered off and dried, resulting in 60.0 g=34.9% and the IR corresponds to the desired product.

Solid 1: Was boiled with 150 mL EtOH and filtered while hot.

By repeated precipitating with KCl, boiling and crystallization, 32 g of the product were obtained for a yield of 19%.

XXIV. Synthesis of 2256

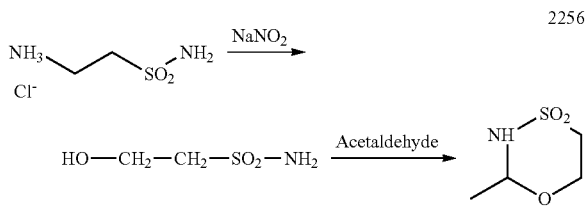

40 g taurinamide hydrochloride, 18 g Sodium nitrite and 300 ml of distilled water were boiled together under reflux until no more gas was created. The clear yellow solution was then cooled to 50° C.

30 ml of 1N NaOH was added to 10.5 g of acetaldehyde. The clear yellow solution was left over the weekend under vacuum to dry. The result was a rust-red honey-like residue weighing 37.6 g, which was extracted with ethyl alcohol. The alcohol solution was filtered and concentrated on a rotary evaporator to dry. The resulting dense oil residue was dissolved with ethyl acetate. The ethyl acetate solution was filtered, and concentrated.

This resulted in 30.7 g of dense oil, rust-like color. From the dense oil, white crystals were isolated. The melting point is about 114-116° C.

The IR spectrum confirmed that the resulting compound had the structure of compound 2256:

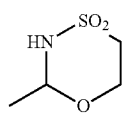

2256

In certain embodiments, a sublimation apparatus, comprised of laboratory glassware known in the art, may be used in a technique of sublimation to purify compounds according to the invention. In certain embodiments, a sublimation vessel is heated under vacuum and under reduced pressure. The compound volatizes and condenses as a purified compound on a cooled surface, leaving non-volatile residue impurities behind. This cooled surface often takes the form of a cold finger. After heating ceases and the vacuum is released, the sublimed compound can be collected from the cooled surface.

In one embodiment, substituted derivatives compound 2250 may be prepared. Substituted derivatives of compound 2250 include:

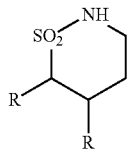

Wherein R may be H or alkyl or aryl. In certain embodiments, R is a $C_1$ to $C_6$ alkyl. In certain embodiments, R is methyl.

In certain embodiments, derivatives of compound 2250 are prepared according to the following reaction scheme:

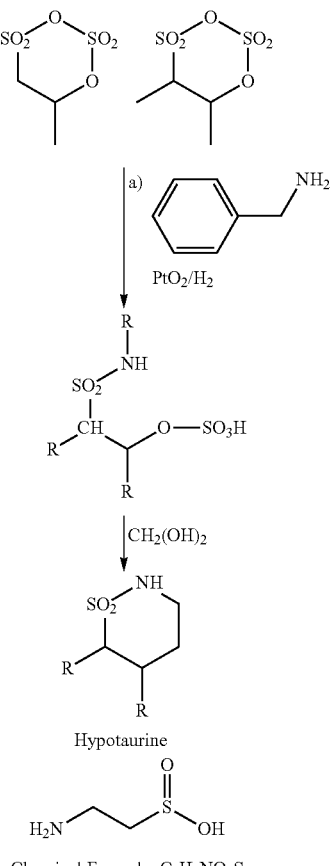

Hypotaurine

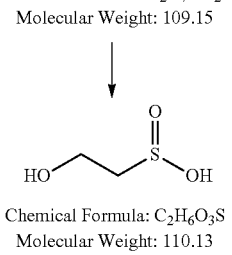

Chemical Formula: $C_2H_7NO_2S$
Molecular Weight: 109.15

Chemical Formula: $C_2H_6O_3S$
Molecular Weight: 110.13

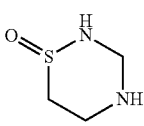

Chemical Formula: $C_3H_8N_2OS$
Molecular Weight: 120.17

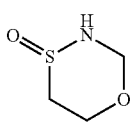

Chemical Formula: $C_3H_7NO_2S$
Molecular Weight: 121.16

Hypotaurultam

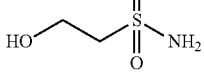

Chemical Formula: $C_2H_7NO_3S$
Molecular Weight: 125.15

IsethionicAmide

| esterification with formic acid

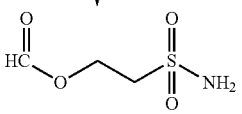

Chemical Formula: $C_3H_7NO_4S$
Molecular Weight: 153.16

2281A

In one embodiment, this disclosure includes a method of killing tumor stem cells by administering to a subject in need thereof a tumor stem cell killing effective amount of taurolidine, taurultam, or a mixture thereof. The tumor stem cell killing effective amount of taurolidine and/or taurultam is less than an amount of taurolidine and/or taurultam required for killing tumor cells.

In some embodiments, the taurolidine, taurultam, or a mixture thereof is administered in a tumor stem cell killing composition at a concentration of about 0.01 to about 500 µg/ml. In some embodiments, the taurolidine, taurultam, or a mixture thereof is administered in a tumor stem cell killing composition at a concentration of about 0.1 to about 100 µg/ml. In some embodiments, the taurolidine, taurultam, or a mixture thereof is administered in a tumor stem cell killing effective composition at a concentration of about 10 to about 50 µg/ml. Taurolidine is effective at killing tumor stem cells in tissue culture in vitro at 0.01 µg/ml.

In some embodiments, the taurolidine, taurultam, or a mixture thereof is administered in a tumor stem cell killing composition at a concentration of about 0.001 to about 2%. In some embodiments, the taurolidine, taurultam, or a mixture thereof is administered in a tumor stem cell killing composition at a concentration of about 0.01 to about 1.5%. In some embodiments, the taurolidine, taurultam, or a mixture thereof is administered in a tumor stem cell killing composition at a concentration of about 0.1% to about 1%.

In one embodiment, the taurolidine, taurultam, or a mixture thereof is administered for tumor stem cell killing to a subject in need thereof at a total daily dose of from about 0.01 g to about 50 g, about 0.1 g to about 30 g, about 0.5 g to about 10 g, or about 1 g to about 5 g.

Tumor stem cell killing effective dosage amounts of the taurolidine, taurultam, or a mixture thereof are dosage units within the range of about 0.01-500 mg/kg, preferably 1-100 mg/kg per day, and most preferably 5-50 mg/kg per day.

In another embodiment, this disclosure includes a method of killing tumor stem cells by administering to a subject in need thereof a compound selected from the following compounds:

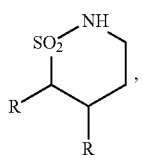

wherein each R is independently H, alkyl, or aryl,

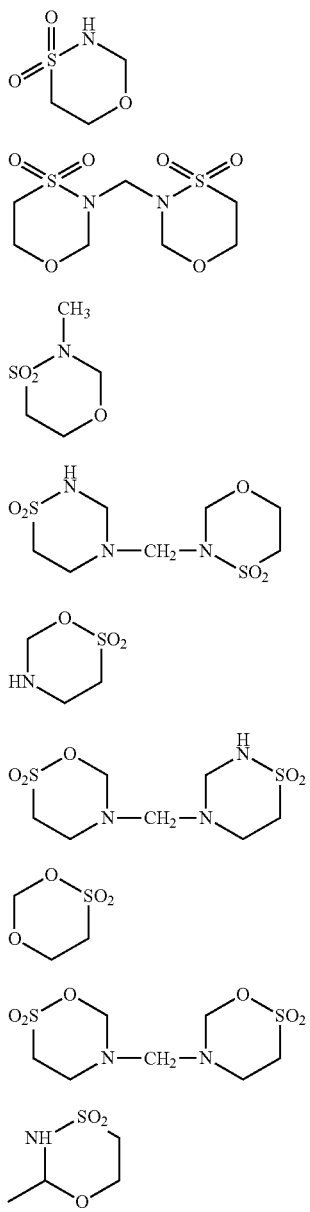

which may be used in combination with taurolidine and/or taurultam. Such a technique provides a method for killing tumor stem cells using at least two compounds having different half-lives, and thereby broadening the pharmacokinetic effects obtained thereby. In one embodiment, compound 2250 may be used in combination with taurolidine and/or taurultam.

EXAMPLES

Example 1

Anti-neoplastic activity of compound 2250

Introduction

Based on the recognition of taurolidine as a powerful anti-neoplastic agent, the analogue 2250 was synthesized by Geistlich Pharma.

Material and Methods

Chemicals: The compound 2250 and taurolidin 2% solution were provided by Geistlich Pharma A G, Wolhusen, assignee of the present invention.

Cell lines: The human glioma cell line LN-229 was used as described previously (Rodak et al. 2005) as well as the human colon adenocarcinoma cell line SW480.

Cytotoxicity assay: Dissociated LN-229 cells were seeded into 96-well plates at a density of $10^4$ cells per well in 100 µl of culture medium. Approximately 24 h later, when the cells had reached 70-80% confluency, the medium was changed and treatment with compound #2250 (4.0-1000 µg/ml), taurolidine (4.0-1000 µg/ml) or standard medium was started. Triplicate cultures were prepared for each sample. After 24 h of incubation at 25° C., the remaining adherent viable cells were stained using crystal violet as described (Rodack et al. 2005). Cell viability was determined by measuring the absorbancy at 540 nm. The results are expressed as killing rate given by the difference between 100% of cells and percentage of cells surviving. $EC_{50}$ values correspond to the concentration inducing 50% cell death.

Results

Positive control: After incubating the human glioblastoma cells (LN-229) for 24 h with taurolidine, a concentration—dependent cytotoxicity was determined (Tab. 1, FIG. 1) with an $EC_{50}$=45 µg/ml, a value which corresponds to earlier results obtained with this cell line (Rodack et al. 2005).

Test of 2250: When 2250 was incubated under the same experimental conditions as taurolidine, a similar concentration-dependent loss of cell viability was observed. The half-maximal concentration of inducing cell death was $EC_{50}$=50 µg/µl (Tab. 1, FIG. 1).

Figure 2:
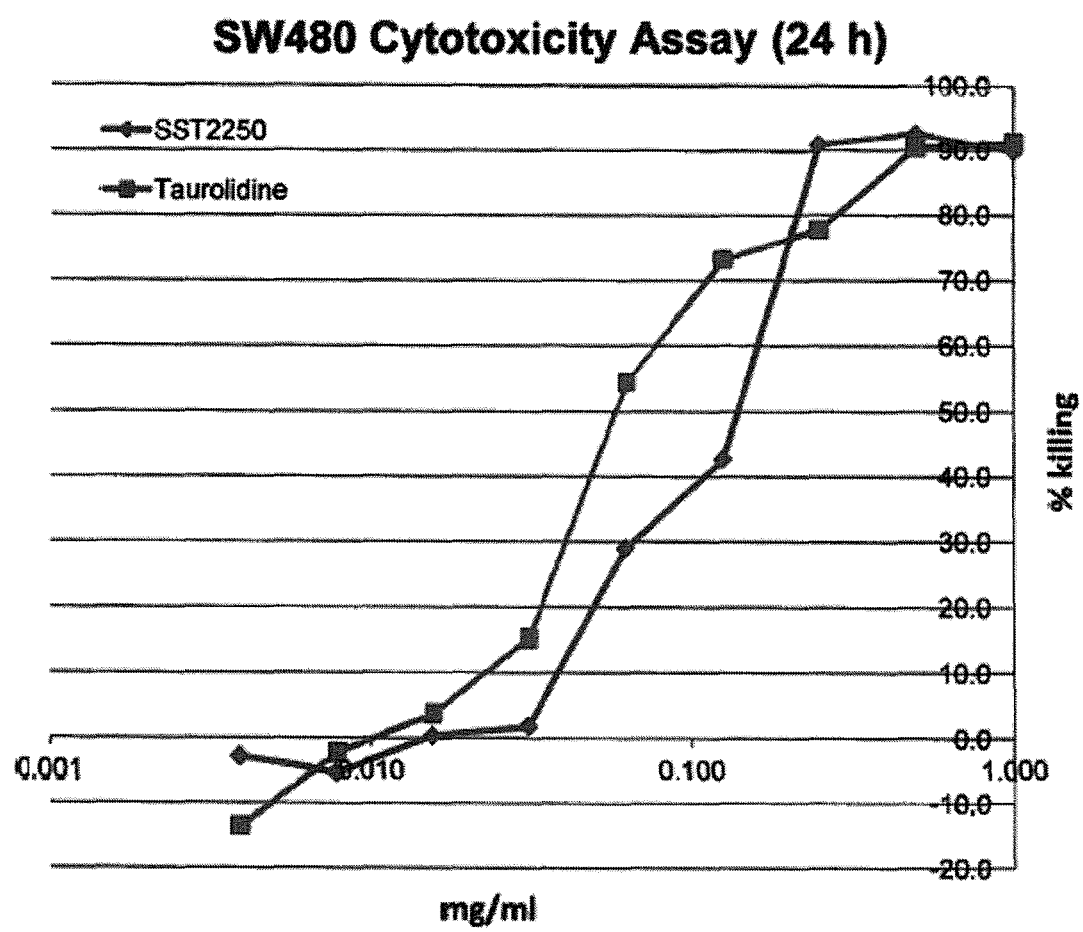
FIG. 2 graphically shows anti-neoplastic activity of one embodiment of the invention in a cytotoxicity assay in SW480 (human colon adenocarcinoma) cells.

The results for SW480 cell cytotoxicities are shown in FIG. 2.

Discussion

The compound 2250 represents a new avenue in the search for novel antineoplastic agents of the taurolidine-type. Biologically, the compound is as potent as taurolidine. Chemically, the compound shows strikingly different features from taurolidine. By replacing a NH group by an ether-oxygen, the double ring structure of taurolidine is avoided. Compound 2250 is a single ring structure and a close structural analogue of taurultam.

Mechanistically, the results show that the antineoplastic activity of taurolidine is unlikely to be due to the formation of a methoxy-derivative, since 2250 is devoid of a methoxy group. The compound causes blebbing of tumor cells.

Summary

The compound 2250 shows potent antineoplastic activity in vitro, as determined for human glioblastoma cells (cell line LN-229). Its potency ($EC_{50}$=45 µg/ml) is comparable to that of taurolidine ($EC_{50}$=50 µg/ml) as tested in the same cell line.

TABLE 1

Cytotoxicity of 2250 and taurolidine against LL-229 glioblastoma cells.

| Concentration µg/ml | 1000 | 500 | 250 | 125 | 62.5 | 31 | 15.5 | 8 | 4 | — |
|---|---|---|---|---|---|---|---|---|---|---|
| Taurolidine OD ± SD | 0.109 ± 0.010 | 0.098 ± 0.007 | 0.165 ± 0.002 | 0.305 ± 0.008 | 0.317 ± 0.008 | 1.132 ± 0.042 | 1.434 ± 0.031 | 1.478 ± 0.040 | 1.530 ± 0.026 | 1.435 ± 0.009 |
| Comp. 2250 OD ± SD | 0.189 ± 0.007 | 0.141 ± 0.007 | 0.120 ± 0.012 | 0.199 ± 0.014 | 0.372 ± 0.006 | 1.482 ± 0.099 | 1.482 ± 0.029 | 1.527 ± 0.033 | 1.477 ± 0.069 | 1.483 ± 0.013 |

The values were measured in triplicate and the OD is the absorbance at 540 nm plus minus standard deviation (SD). High values correspond to high cell viability.

Example 2

The new compound 2250 (Tetrahydro1,4,5-oxathizain-4-dioxid) was tested and found to have a very high level of antibacterial activity against *Staphylococcus aureus* and *Escherichia coli*. The antibacterial activity against *Staph. aureus* is about double as high as Taurultam.

Example 3

In punch plate tests, Compound 2250 was tested and found highly active against MRSA lines 188, 189, 193, 194 and 195.

By displaying a combination of antimicrobial and antineoplastic activity, compound 2250 is particularly suitable for surgical oncology.

Example 4

Each of compounds identified herein as compound 2250, 2255, 2245, A1, A3, B1, B2, or B3 is tested against cancer cell lines of cancers identified herein, and found to be active against such cell lines.

Example 5

Each of compounds identified herein as compound 2250, 2255, 2245, A1, A3, B1, B2, or B3 is administered to patients having cancers identified herein, and is found to be effective in treating such cancers and safe for use in patients. Each of these compounds is administered with Vitamin D3, a derivative, metabolite or analog thereof and the combination is found to increase the anti-tumor effects of the compounds.

Example 6

The half-life of compound 2250 in human fresh blood was measured at 37° C. in vitro by GC, PYE Unicam Series 204 FID.
Baseline Value: 49.0 ppm
After 1 hour: 50.6 ppm
After 2 hours: 47.6 ppm
After 20 hours: 38.6-39.0 ppm.

Thus, the half-life of compound 2250 is greater than 24 hours in human blood, which is significantly higher than the half-life of taurolidine, which was found to be ~30 minutes using the same test.

Example 7

Tissue samples from high grade gliomas WHO grade IV from newly diagnosed patients (medium age of 54±10 years) were minced mechanically, digested enzymatically and the dissociated cells were filtered. The isolated tumor cells were cultured as bulk cells. Cancer Stem Cells (CSCs) were isolated by the formation of neurospheres under neurosphere conditions (using neurobasal medium) from the murine SMA 560 glioma cell line or from freshly isolated human glioblastoma cells.

Cytotoxicity Assay

Figure 3A:
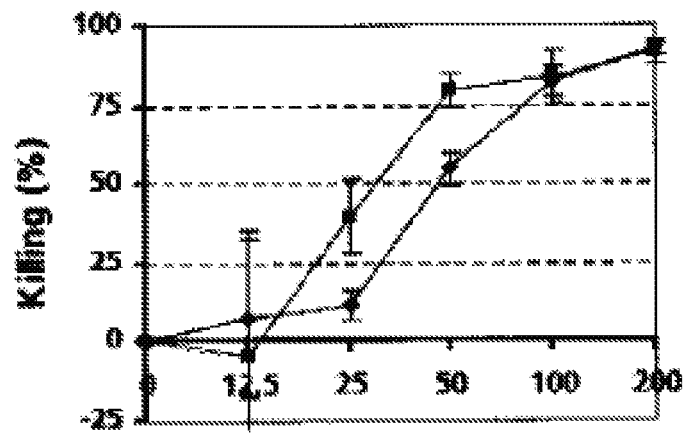
FIG. 3A-3C Cytotoxicity induced in murine SMA 560 bulk glioma cells after treatment with taurolidine and taurultam (TT). Cytotoxicity was assessed after 24 h (FIG. 3A) and 48 h (FIG. 3B) of treatment. The $EC_{50}$ values for taurolidine (34.6 µg/ml) and taurultam (19.3 µg/ml) are given in the lower panel (FIG. 3C). Data are presented as mean values±SD of three independent experiments.
Figure 3B:
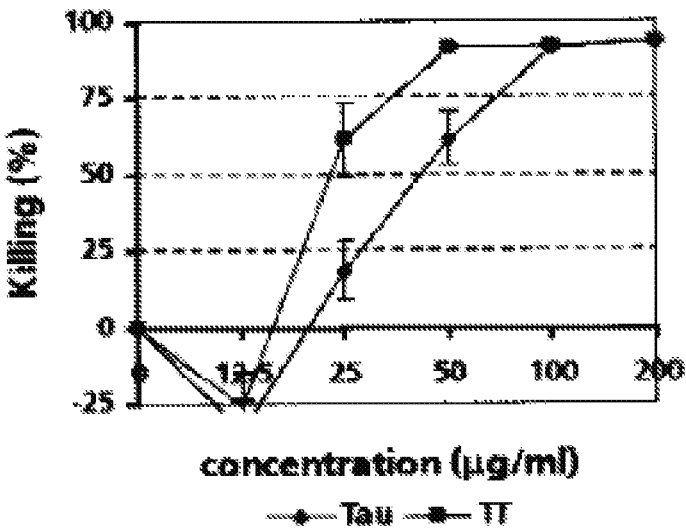
Figure 3C:
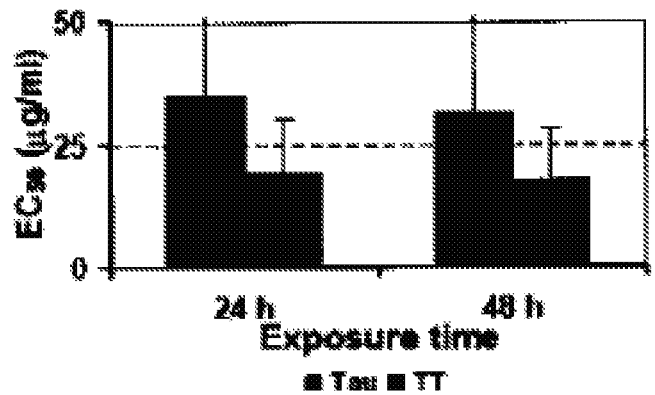
Figure 4:
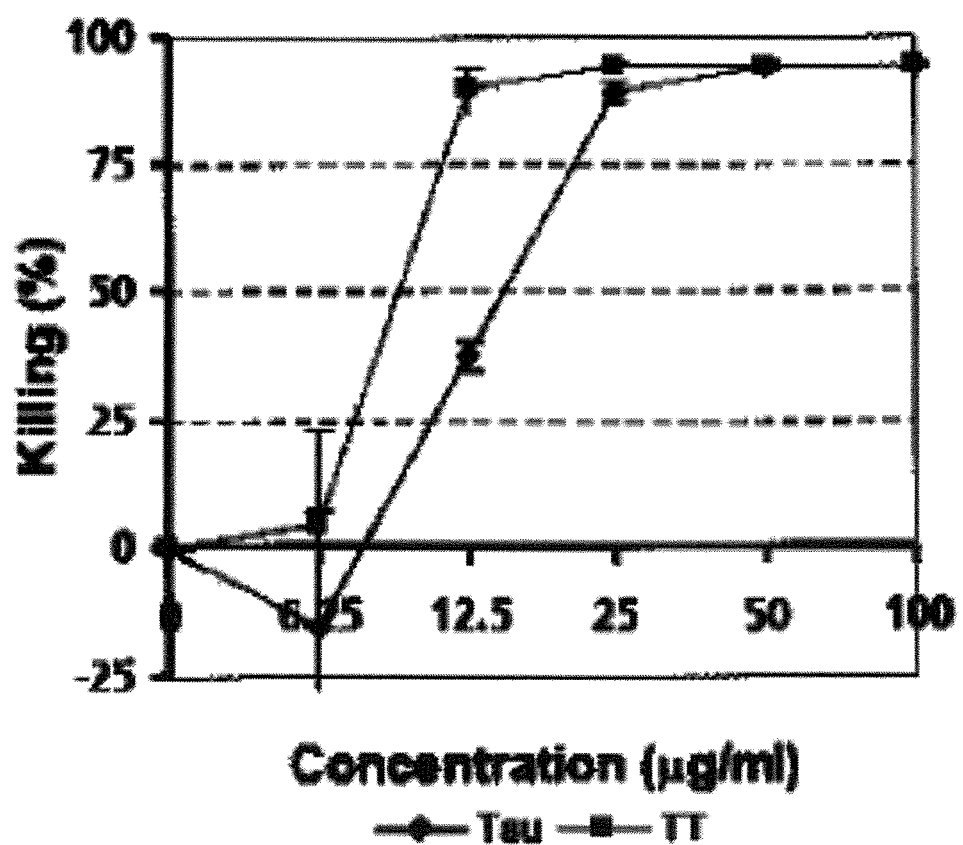
FIG. 4 Cytotoxicity induced by taurolidine and taurultam (TT) in murine SMA560 glioma cancer stem cells (CSC). Data are presented as mean values±SD.

Bulk glioma tumor cells were cultured and incubated with taurolidine or taurultam for 24 h or 48 h as described previously (Rodak et al., J. Neurosurg. 102, 1055-1068, 2005). CSCs were cultured for 7 days and subsequently exposed to taurolidine, taurultam or temozolamide for 24 hours. The number of remaining adherent cells were stained (crystal violet or Alamar Blue) and quantified by absorbance measurements (540 nm). Cell survival was expressed as the percentage of cells surviving relative to the number of cells surviving in untreated control cultures. The results are given as % killing rate or $EC_{50}$ as the dose required for half-maximal cytotoxicity. Results Cytotoxicity of Taurolidine and Taurultam against Cancer Cells and Cancer Stem Cells from the Mouse The mouse SMA560 glioma cell line was used to provide tumor bulk cells and CSCs. Following incubation of SMA560 bulk cells with various concentrations of taurolidine and taurultam (6.25, 12.5, 25, 50, 100, 200 µg/ml), cytotoxicity was determined after 24 h and 48 h of incubation. For both taurolidine and taurultam, a clear dose-dependent cytotoxicity was found with no major difference in potency between the 24 h and 48 h time of incubation (FIG. 3A,B). The $EC_{50}$ value was 34.6 µg/ml for taurolidine and 19.3 µg/ml for taurultam (FIG. 3C). Mouse CSCs were generated from the SMA560 glioma cell line and cultured for 7 days. The CSCs were treated with the same concentration of taurolidine and taurultam as above and cytotoxicity was determined after 24 hours. As shown in FIG. 4, both taurolidine and taurultam showed a dose-dependent cytotoxicity with an $EC_{50}$ of 12.5 µg/ml for taurolidine and $EC_{50}$ of 10 µg/ml for taurultam against murine CSCs. These values demonstrate for the first time that taurolidine and taurultam are effective against a CSC.

Figure 5A:
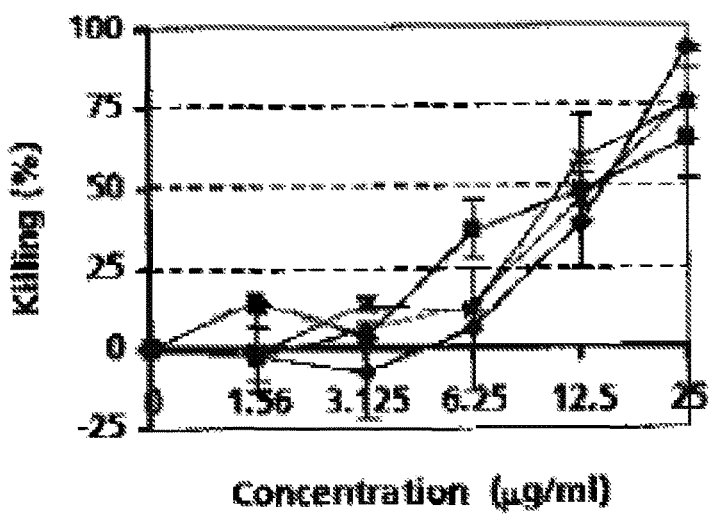
FIG. 5A-5C Cytotoxicity induced in cancer stem cells isolated from four glioblastoma multiforme (GBM) patients (GBM #3, #4, #5 and #6) after treatment for 24 h with taurolidine (FIG. 5A), taurultam (TT) (FIG. 5B) or temozolamide (FIG. 5C). Data are presented as mean values±SD.
Figure 5B:
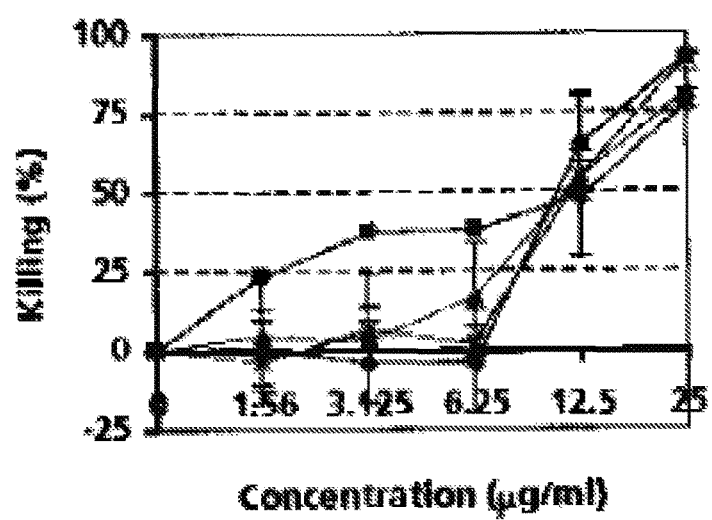
Figure 5C:
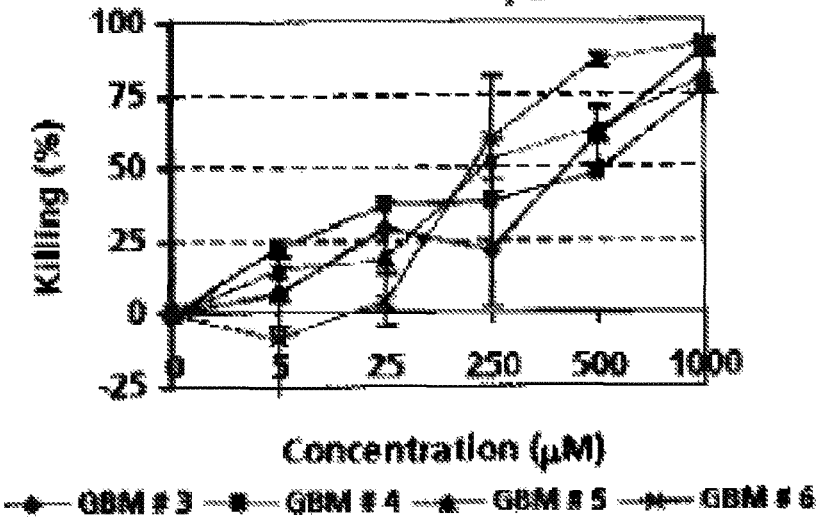
Figure 6:
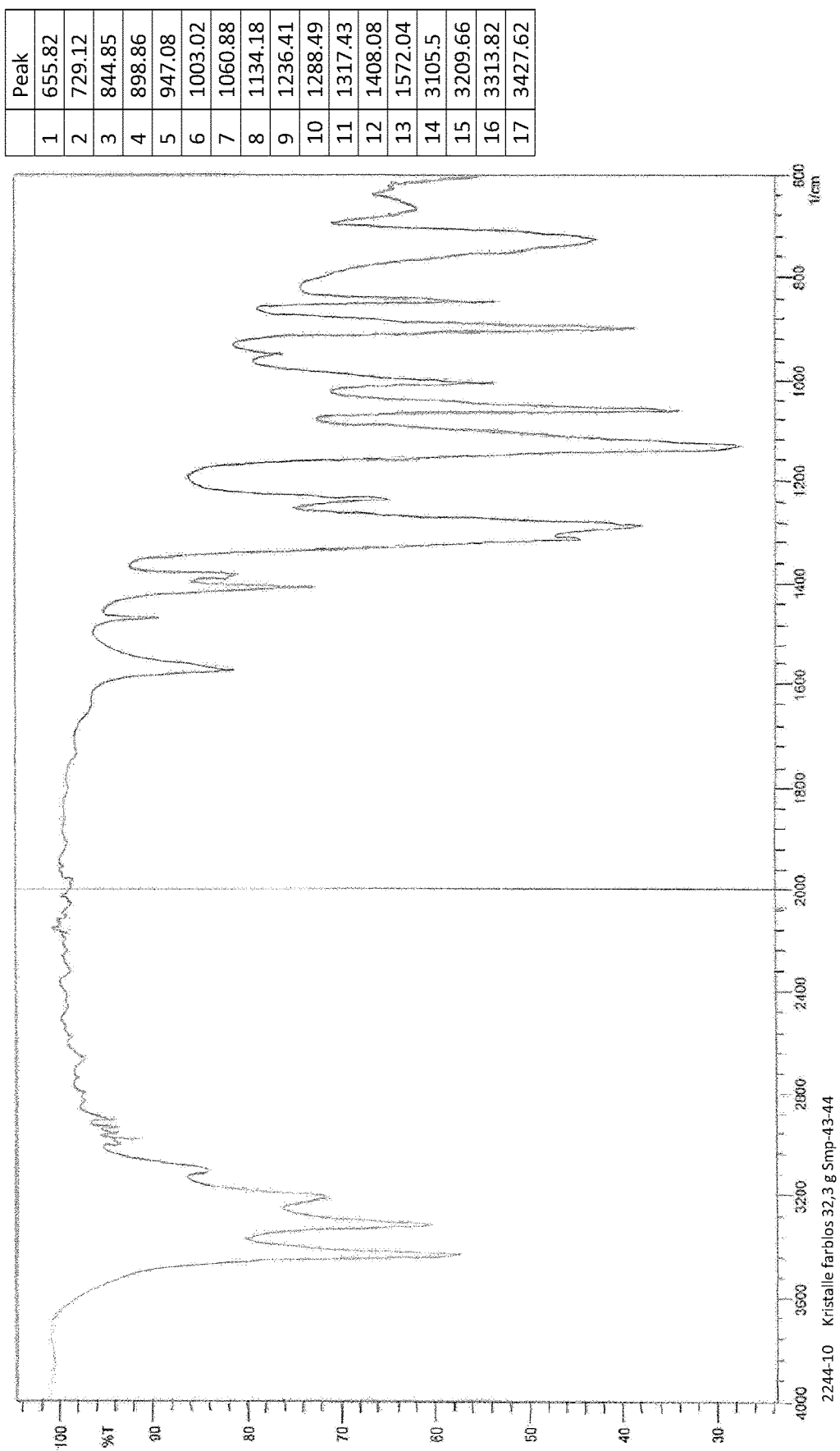
FIG. 6 FTIR spectrum of compound 2244 made according to the present invention.

Taurolidine and Taurultam Induce Cell Death in Human CSC Isolated from Four Different Glioblastoma Patients CSCs were isolated from glioblastoma tissue resected from four patients. The same range of concentrations of taurolidine and taurultam was applied as above and the cytotoxicity was measured after 24 hours of incubation with drug. All four glioblastoma CSCs tested (GBM #3, #4, #5 and #6) were similarly sensitive to taurolidine and taurultam (FIG. 5A,B). The mean $EC_{50}$ value of taurolidine was 13±2 µg/ml, the $EC_{50}$ value of taurultam was 11±1.4 µg/ml (Table 2). In these experiments, the cytotoxic capacity of taurolidine and taurultam was compared with that of temozolamide (TIM) applied in the concentration range of 5 µM to 1,000

μM (FIG. 2C). The mean $EC_{50}$ value of TMZ was 68.5±26 μg/ml (Table 2). Interestingly, this concentration is much higher than peak plasma levels of TMZ measured in patients (13.7 μg/ml) (Portnow et al., Clin Cancer Res 15, 7092-7098, 2009).

The results demonstrate that both taurolidine and taurultam are effective against CSCs and this finding was established for glioma CSCs from two species, mouse and man.

The mouse CSCs were generated from a mouse glioma cell line (SMA 560). Remarkably, based on the $EC_{50}$ values, the CSCs were even more sensitive to taurolidine and taurultam than the corresponding glioma bulk cells (about 3 fold for taurolidine and 2 fold for taurultam) (FIGS. 3, 4).

Human CSCs, freshly isolated from four human glioblastoma patients, were likewise highly chemosensitive to both taurolidine and taurultam. The $EC_{50}$ values for cytotoxicity were 13±2 ug/ml and 11±1.4 μg/ml, respectively (Table 2). These values demonstrate that the human CSCs, like their murine counterparts, are more sensitive to taurolidine and taurultam (about 3 to 4 fold) than the human glioblastoma bulk cells which display $EC_{50}$ values in the range of 50 μg/ml (Rodak et al., J. Neurosurg., 102, 1055-68, 2005).

TABLE 2

Cytotoxicity Induced by taurolidine (Tau), taurultam (TT) or temozolamide (TMZ) in cancer stem cells (CSC) derived from four glioblastoma patients. $EC_{50}$ (μg/ml) = drug concentration resulting in 50% cell death compared to untreated control cultures in vitro.

| Cancer Stem Cells | n | Cytotoxicity $EC_{50}$ (μg/ml) 24 h | | |
|---|---|---|---|---|
| | | Taurolidine | Taurultam | Temozolamide |
| GBM #3 | 3 | 15 | 10.5 | 84.4 (435 μM) |
| GBM #4 | 2 | 12.5 | 12.5 | 97 (500 μM) |
| GBM #5 | 2 | 14 | 11 | 48.5 (250 μM) |
| GBM #6 | 3 | 10 | 9 | 44 (230 μM) |
| Mean ± SD | | 13 ± 2 | 11 ± 1.4 | 68.5 ± 26 |

Example 8

Taurolidine and taurultam were tested against cancer stem cells derived from a murine glioma cell line and human cancer stem cells. Taurolidine and taurultam were found to exert potent anti-neoplastic activity against cancer stem cells derived from a murine glioma cell line ($EC_{50}$=12.5 μg/ml for taurolidine, $EC_{50}$=10 μg/ml for taurultam) as well as against human cancer stem cells, freshly isolated from four glioblastoma patients ($EC_{50}$=13±2 μg/ml for taurolidine; $EC_{50}$=11±1.4 μg/ml for taurultam).

Example 9

Antineoplastic Effect on Pancreatic Stem Cell-Like Multicellular Spheroid Cultures.

Multicellular spheroids are composed of tumor cells growing in a 3-dimensional structure stimulating the growth, micro-environmental conditions and stem cell-like characteristics of real tumors. The multicellular tumor spheroid (MCTS) model compensates for many of the deficiencies seen in monolayer cultures. Spheroids on the scale of 200-500 μm develop chemical gradients of oxygen, nutrients, and catabolites, while having morphological and functional features similar to tumors. Therefore, assays utilizing the MCTS model allow for the assessment of drug penetration and are more predictive of in vivo success compared with monolayer cultures. MCTS assays are a tumor model system of intermediate complexity between standard monolayer and tumors in vivo.

Pancreatic tumor cells (Panc Tu-1, BxPC-3, Mia Paca-2, ASPC1) and pancreatic primary tumor cells (Bo80) were seeded in ultra-low adhesion plates in special stem cell media.

Pancreatic tumor cells (ASPC1, Mia Paca-2, Panc Tul, BxPC-3) and pancreatic primary tumor cells (Bo80) were raised in monolayer culture before seeding in ultra low adhesion plates under conditions of special stem cell media to form multicellular spheroids and passed through a cell strainer to exclude aggregates.

Half-maximal inhibition of cell viability was achieved with 750-1000 μM of compound 2250 in tumor cell lines AsPC-1, BxPC-3 and HCT-116. These effects are similar to those observed in glioma cell line LN-229. The induction of cell death was due to apoptosis and necrosis (most likely necroptosis). It was found that the induction of this programmed cell death was prevented by addition of the reducing agent N-acetylcysteine and that caspases are not involved. Thus, there is a redox-directed mechanism of action.

The growth of pancreas tumor cells (AsPC-1, BxPC-3 and HCT-116) was inhibited by compound 2250 with a half-maximal concentration of 300 μM, which is considerably lower than the concentration needed to elicit cytotoxicity.

As shown in FIG. 8, multicellular pancreatic tumor (Panc Tul or BxPC-3) spheroids were tested as control, taurolidine-treated (500 μM) or compound 2250-treated (1000 μM) samples for 48 hours (columns labeled A). After treatment, each of the whole cell suspensions was passed through a 45 μm cell strainer again to analyze residual aggregates for their stability (columns labeled B).

Figure 9A:
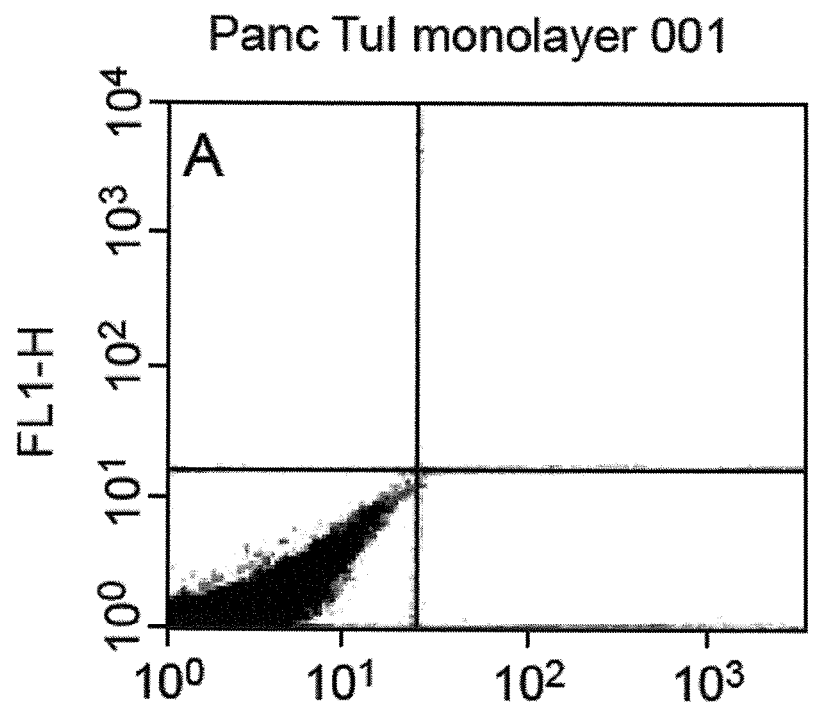
FIGS. 9A and 9B show the results of FACS analysis of the Panc Tu1 multicellular spheroid cultures CD133 content.
Figure 9B:
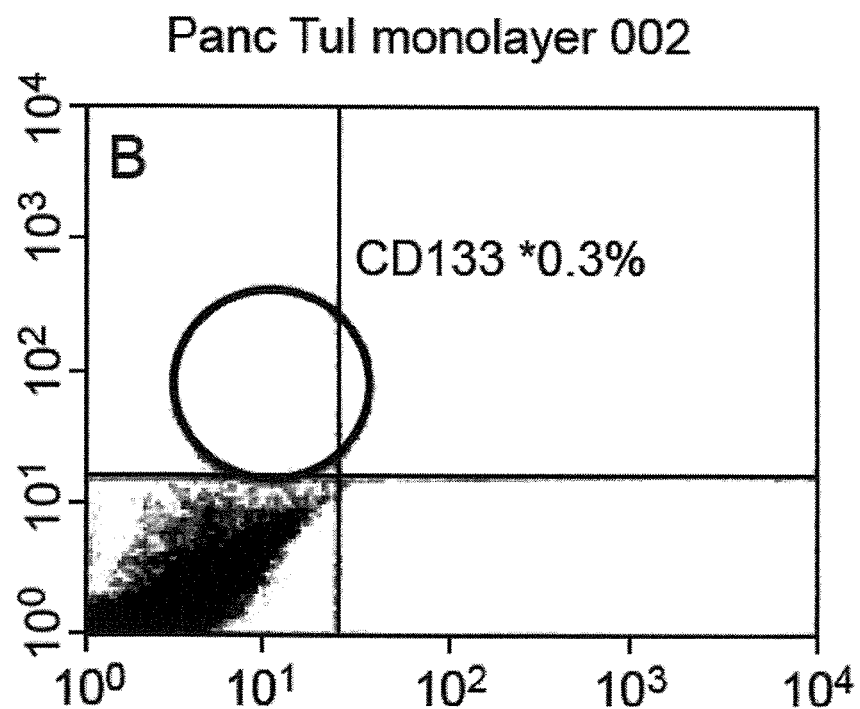

FIGS. 9A and 9B show the results of FACS analysis of the Panc Tul multicellular spheroid cultures CD133 content. CD133 is a known and well-established hallmark of stem cells. The results show that the amount of CD133-positive cells in multicellular spheroid cultures of Panc Tul was enriched 10-fold compared to Panc Tul grown in monolayer culture (B). Isotype IgG was used as negative control (A). The results demonstrate that taurolidine and compound 2250 have an antineoplastic effect on the pancreatic stem cell like multicellular spheroid cultures.

Example 10

In vivo study of taurolidine and compound 2250 as antineoplastic agents in malignant pancreatic carcinoma.

The effects of taurolidine and compound 2250 were analyzed on nude mice (NMRI-Foxn1 nu/nu). $1 \times 10^7$ tumor cells (PancTu-I and MiaPaca 2) were injected subcutaneously into the flank. The animals were randomized into three groups: the control group; the group treated i.p. with taurolidine (TRD), and the group treated i.p. with compound 2250 (NDTRLT).

Tumors were grown to a size of 200 mm³ before the treatment was started. Mice were treated on alternating days with 500 mg/kg*body weight (BW).

Figure 10A:
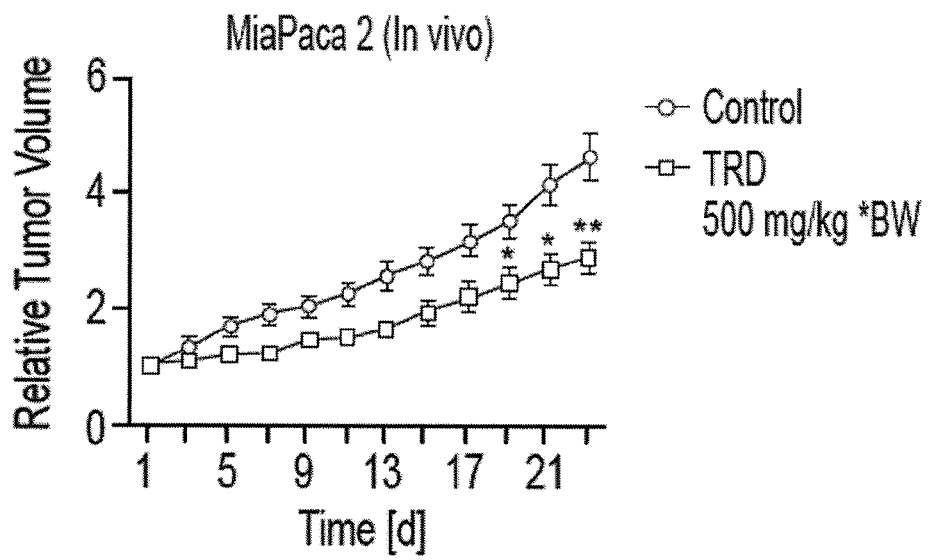
FIG. 10A shows MiaPaca2 tumor volume upon treatment with control or taurolidine.

As shown in FIG. 10A, administration of taurolidine decreased MiaPaca2 tumor volume significantly compared to control (by about 2-fold).

Figure 10B:
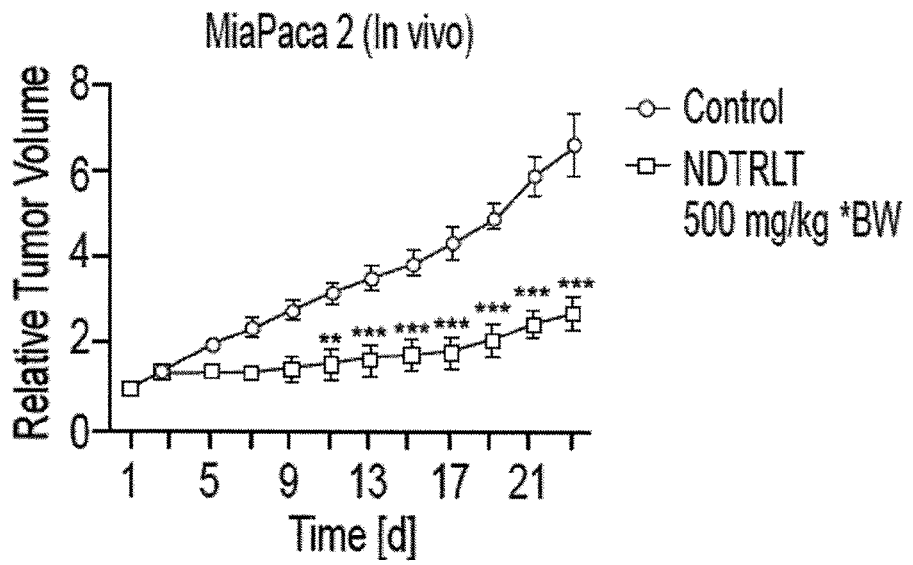
FIG. 10B shows MiaPaca2 tumor volume upon treatment with control or compound 2250.

As shown in FIG. 10B, administration of compound 2250 decreased MiaPaca2 tumor volume significantly compared to control (by over 3-fold).

Figure 10C:
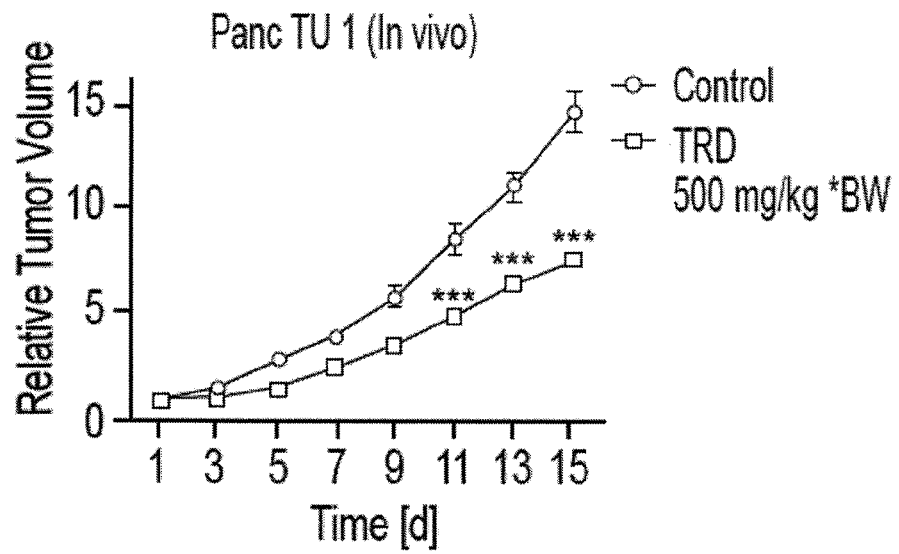
FIG. 10C shows PancTu I tumor volume upon treatment with control or taurolidine.

As shown in FIG. 10C, administration of taurolidine decreased PancTu I tumor volume significantly compared to control (by about 3-fold).

Figure 10D:
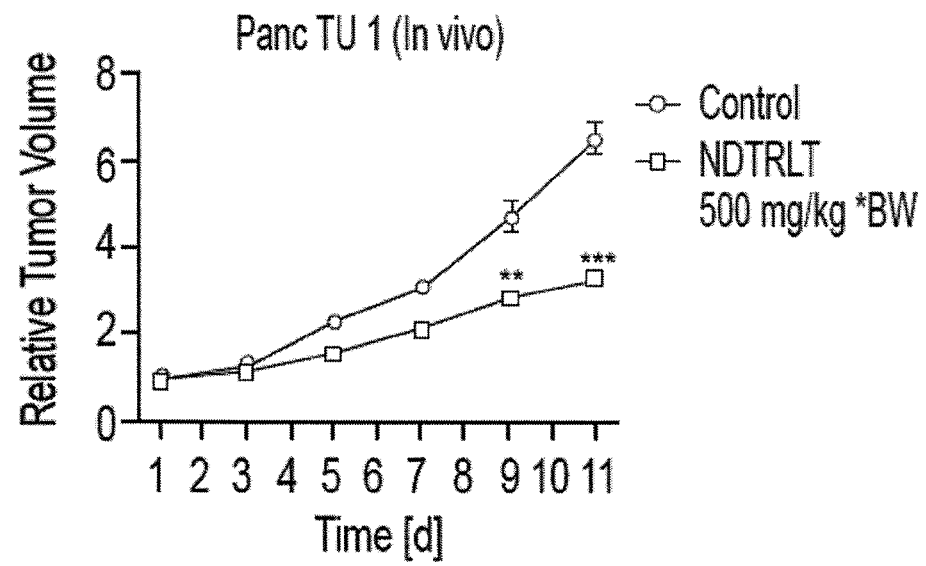
FIG. 10D shows PancTu I tumor volume upon treatment with control or compound 2250.

As shown in FIG. 10D, administration of compound 2250 decreased PancTu I tumor volume significantly compared to control (by about 2-fold).

The applied taurolidine and compound 2250 dosages showed no toxic effect on the mice during the study. In both tumor cell line models, a significant reduction of tumor growth was obtained.

Tumor growth (volume) was significantly reduced from day 9 onwards (PancTu1) and day 11 onwards (MiaPaca2) versus controls. The dose of 500 mg/kg i.p. was well tolerated with no overt sign of toxicity.

Figure 11A:
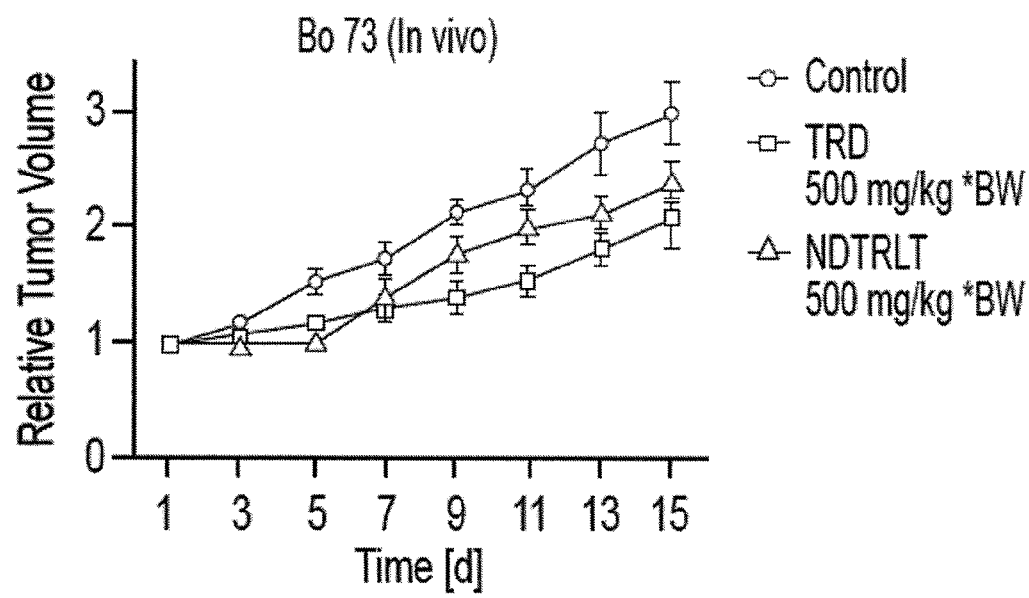
FIG. 11A is a xenograft model of pancreatic primary tumors (Bo 73) observed for 15 days when treated with control, taurolidine or compound 2250.
Figure 11B:
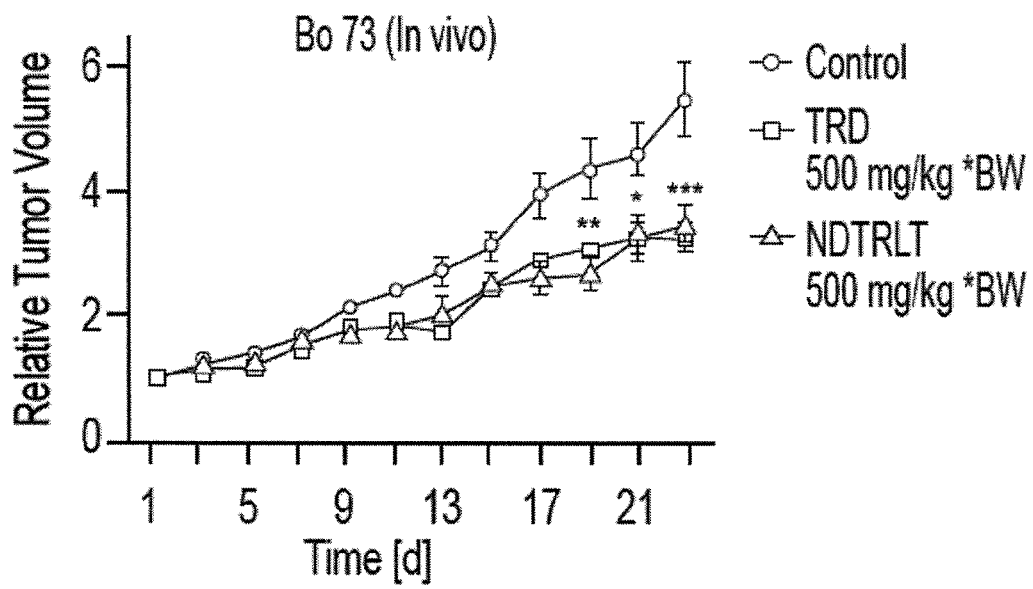
FIG. 11B is a xenograft model of pancreatic primary tumors (Bo 70) observed for 23 days when treated with control, taurolidine or compound 2250.

As shown in FIG. 11A, a xenograft model of pancreatic primary tumors (Bo 73) was observed for 15 days and it was found that administration of taurolidine slightly reduced relative tumor volume compared to control and administration of compound 2250 further reduced relative tumor volume compared to control. However, the differences in tumor volumes were not statistically relevant, likely due to the short duration of the study and the slow growth rate of the tumors. In FIG. 11B, a xenograft model of pancreatic primary tumors (Bo 70) was observed for 23 days and it was observed that administration of taurolidine and compound 2250 significantly reduce tumor volume compared to control.

Administration, e.g., intraperitoneally, of taurolidine and/or compound 2250 inhibits tumor growth in vivo.

What is claimed is:

1. A method for producing compound 2260 comprising the following reaction:

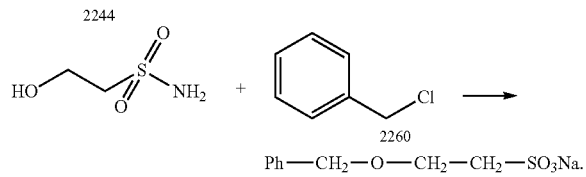

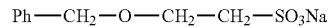

2. A process for producing

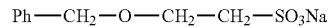

(sodium 2-benzyletherethane sulfonate) comprising the following reaction:

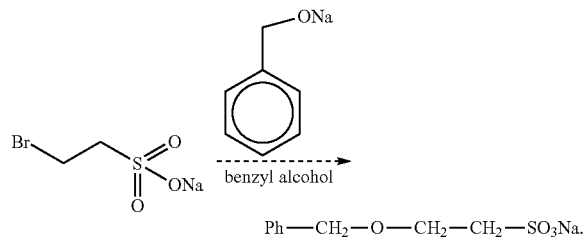

3. The process of claim 2, wherein the process comprises adding sodium 2-bromoethanesulfonate to a solution of benzyl alcohol and sodium benzyloxide to form a mixture, boiling the mixture to reflux four times, concentrating under vacuum until dry, boiling with ethyl alcohol, filtering the ethyl alcohol, and concentrating to dryness to obtain solid sodium 2-benzyletherethanesulfonate.

4. The process of claim 3, further comprising boiling said solid sodium 2-benzylether ethanesulfonate in ethyl alcohol, filtering, then cooling to obtain sodium 2-benzylether ethanesulfonate crystals having increased purity.

5. A process for producing a compound having the formula

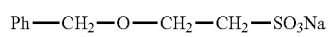

comprising the following reaction:

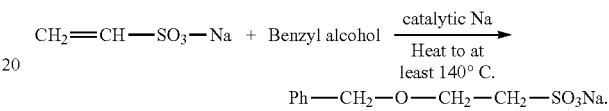

6. The process of claim 5, which comprises the following steps sequentially: adding vinylsulphonic acid sodium to a solution of benzyl alcohol and a catalytic amount of sodium to form a mixture, warming the mixture with stirring to dissolve most or all of the vinylsulphonic acid sodium, cooling the warmed mixture to obtain crystals, vacuum filtering the crystals, suspending the filtered crystals in ethyl alcohol, vacuum filtering the suspended crystals, and drying the vacuum filtered crystals to obtain

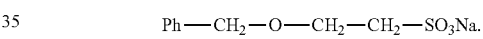

7. A method for producing

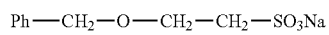

comprising the following reaction:

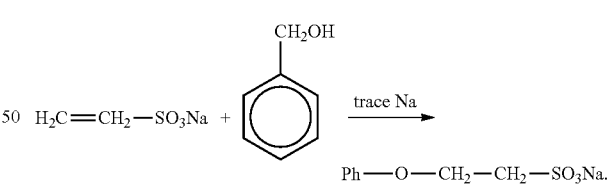

8. The process of claim 7, which comprises the following steps sequentially: adding vinylsulphonic acid sodium to a solution of benzyl alcohol and a trace amount of sodium, stirring the mixture under reflux, distilling off the benzyl alcohol under vacuum, boiling the remainder with alcohol, filtering the alcohol, concentrating the alcohol and crystallizing the resulting reaction product to obtain

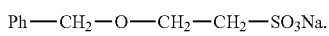

9. A process for producing a

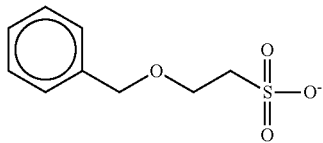

alkali metal cation comprising the following reaction:

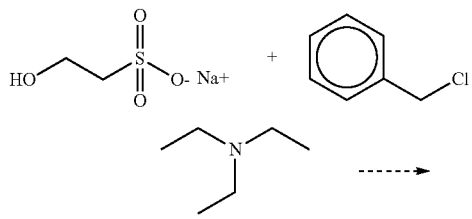

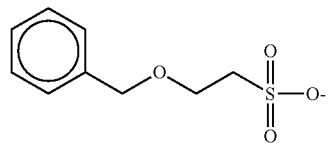

alkali metal cation.

10. The process of claim 9, comprising the following steps sequentially: mixing isethionic acid sodium salt with benzyl chloride, heating the mixture, adding triethylamine dropwise to the mixture, cooling the mixture, adding water to the mixture and stirring to obtain an aqueous phase and an organic phase, separating the aqueous phase from the organic phase, washing the aqueous phase with dichloromethane, adding KCl to the aqueous phase, filtering, refrigerating the aqueous phase, extracting remaining solid, treating the aqueous phase with KCl, refrigerating the aqueous phase, filtering off solid product from the aqueous phase and drying the solid to obtain

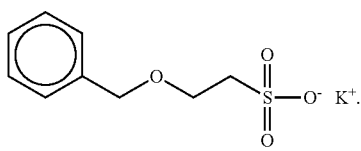

11. A method for producing a

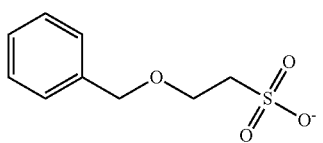 [SMILES: O=S(=O)([O-])CCOCc1ccccc1]

alkali metal cation comprising the following reaction:

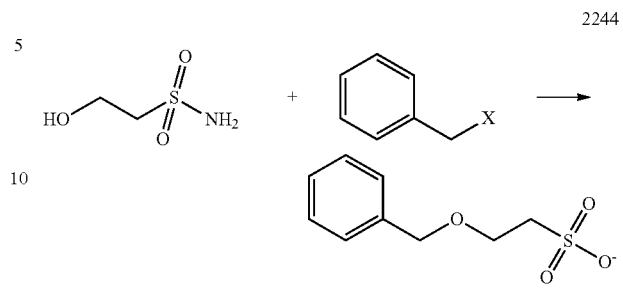

alkali metal cation, wherein X is a leaving group.

12. A process for producing a

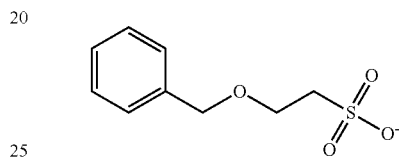

salt comprising the following reaction:

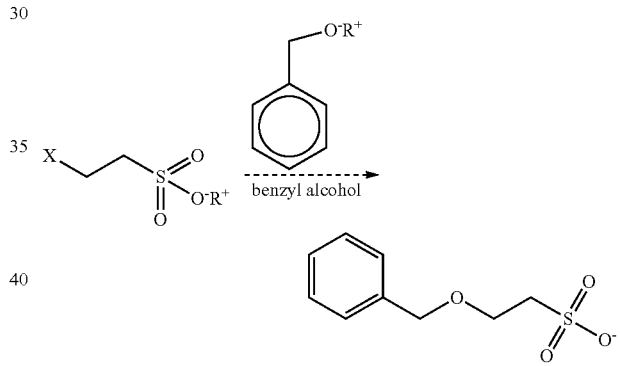

salt, wherein X is a leaving group and each R is, independently, an alkali metal.

13. The process of claim 12, wherein the process comprises adding a 2-haloethanesulfonate salt to a solution of benzyl alcohol and an alkali metal salt of benzyloxide to form a mixture, boiling the mixture to reflux, concentrating under vacuum until dry, boiling with an alcohol, filtering the alcohol, and concentrating to obtain solid 2-benzyletherethanesulfonate salt.

14. The process of claim 13, further comprising boiling said solid 2-benzylether ethanesulfonate salt in alcohol, filtering, then cooling to obtain 2-benzylether ethanesulfonate salt crystals having increased purity.

15. A process for producing a compound having the formula

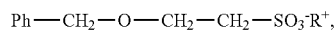

comprising the following reaction:

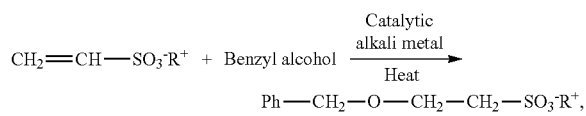

wherein each R is independently an alkali metal.

16. The process of claim 15, which comprises the following steps sequentially: adding vinylsulphonic acid salt to a solution of benzyl alcohol and a catalytic amount of an alkali metal to form a mixture, warming the mixture with stirring to dissolve most or all of the vinylsulphonic acid salt, cooling the warmed mixture to obtain crystals, vacuum filtering the crystals, suspending the filtered crystals in alcohol, vacuum filtering the suspended crystals, and drying the vacuum filtered crystals to obtain

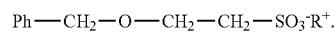

17. A method for producing

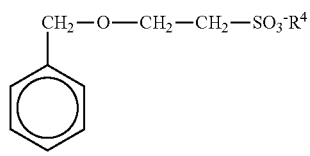

comprising the following reaction:

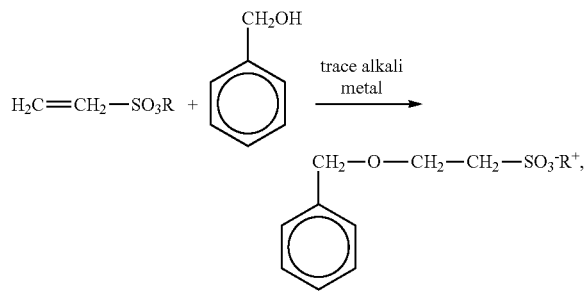

wherein each R is independently an alkali metal.

18. The process of claim 17, which comprises the following steps sequentially: adding vinylsulphonic acid salt to a solution of benzyl alcohol and a trace amount of an alkali metal, stirring the mixture under reflux, distilling off the benzyl alcohol under vacuum, boiling the remainder with alcohol, filtering the alcohol, concentrating the alcohol and crystallizing the resulting reaction product to obtain

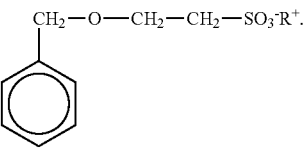

19. A process for producing

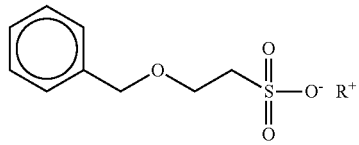

comprising the following reaction:

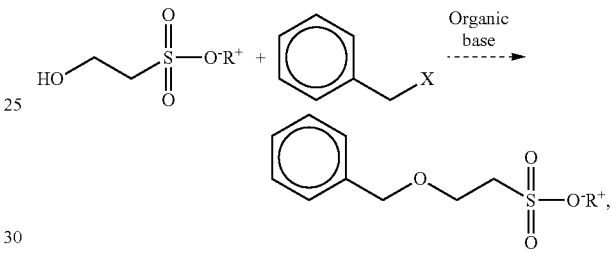

wherein X is a leaving group and wherein R is an alkali metal.

20. The process of claim 19, comprising the following steps sequentially: mixing isethionic acid salt with benzyl halide, heating the mixture, adding an organic base to the mixture, cooling the mixture, adding water to the mixture and stirring to obtain an aqueous phase and an organic phase, separating the aqueous phase from the organic phase, washing the aqueous phase with dichloromethane, adding a first inorganic salt to the aqueous phase, filtering, refrigerating the aqueous phase, extracting remaining solid, treating the aqueous phase with the first inorganic salt or a second inorganic salt, refrigerating the aqueous phase, filtering off solid product from the aqueous phase and drying the solid to obtain

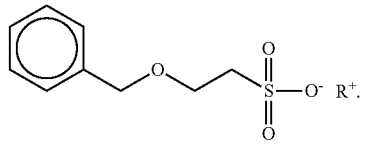

* * * * *